(12) United States Patent
Banowski et al.

(10) Patent No.: US 8,603,445 B2
(45) Date of Patent: *Dec. 10, 2013

(54) WATER-FREE ANTIPERSPIRANT SPRAYS IN WHICH ACTIVE SUBSTANCES ARE MORE READILY RELEASED

(75) Inventors: Bernhard Banowski, Dusseldorf (DE); Nadine Buse, Hilden (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/418,628

(22) Filed: Mar. 13, 2012

(65) Prior Publication Data

US 2012/0171143 A1   Jul. 5, 2012

Related U.S. Application Data

(63) Continuation of application No. PCT/EP2010/063568, filed on Sep. 15, 2010.

(30) Foreign Application Priority Data

Sep. 22, 2009   (DE) .......................... 10 2009 029 669

(51) Int. Cl.
*A61K 8/00*   (2006.01)

(52) U.S. Cl.
USPC ......................................................... 424/65

(58) Field of Classification Search
None
See application file for complete search history.

(56) References Cited

U.S. PATENT DOCUMENTS

| | | | |
|---|---|---|---|
| 2,571,030 A | 10/1951 | Govett et al. | |
| 3,887,692 A | 6/1975 | Gilman | |
| 3,904,741 A | 9/1975 | Jones et al. | |
| 4,359,456 A | 11/1982 | Gosling et al. | |
| 4,479,887 A | 10/1984 | Seibert | |
| 4,775,528 A | 10/1988 | Callaghan et al. | |
| 5,017,360 A | 5/1991 | Katsoulis | |
| 5,080,830 A | 1/1992 | Damaso | |
| 5,118,497 A | 6/1992 | Katsoulis | |
| 5,643,558 A | 7/1997 | Provancal et al. | |
| 5,833,964 A * | 11/1998 | Linn et al. | 424/65 |
| 6,010,688 A | 1/2000 | Shen | |
| 6,042,816 A | 3/2000 | Shen | |
| 6,074,632 A | 6/2000 | Shen | |
| 6,245,325 B1 | 6/2001 | Shen | |
| 6,613,338 B1 | 9/2003 | Schreiber et al. | |
| 6,663,854 B1 | 12/2003 | Shen et al. | |
| 6,902,723 B2 | 6/2005 | Shen | |
| 2001/0051138 A1 | 12/2001 | Scafidi et al. | |
| 2004/0009133 A1 | 1/2004 | Kolodzik et al. | |

FOREIGN PATENT DOCUMENTS

| | | |
|---|---|---|
| DE | 19501288 A1 | 7/1996 |
| DE | 19756454 C1 | 6/1999 |
| GB | 1347950 A | 2/1974 |
| GB | 2048229 A | 12/1980 |
| WO | WO 98/17238 A1 | 4/1998 |
| WO | WO 2009/083547 A2 | 7/2009 |
| WO | WO 2009/083807 A2 | 7/2009 |

OTHER PUBLICATIONS

PCT International Search Report (PCT/EP2010/063568) dated Feb. 21, 2011.

* cited by examiner

*Primary Examiner* — Paul Dickinson
(74) *Attorney, Agent, or Firm* — David K. Benson

(57) ABSTRACT

Antiperspirant compositions for personal body care which are produced as a suspension or solution that can be sprayed with or without using a propellant include at least one antiperspirant, at least one oil as a carrier, the oil being liquid in normal conditions, 0-7 percent by weight of free water relative to the weight of the composition, and at least one selected alkyl-modified polyether.

13 Claims, No Drawings

WATER-FREE ANTIPERSPIRANT SPRAYS IN WHICH ACTIVE SUBSTANCES ARE MORE READILY RELEASED

CROSS-REFERENCES TO RELATED APPLICATIONS

This application is a continuation of PCT/EP2010/063568, filed on Sep. 15, 2010, which claims priority under 35 U.S.C. §119 to DE 10 2009 029 669.7 filed on Sep. 22, 2009, both of which are hereby incorporated by reference.

FIELD OF THE INVENTION

The present invention generally relates to water-free antiperspirant compositions, and particularly relates to water-free antiperspirant suspensions which are sprayable with or without a propellant, and which allow active substance release of the active antiperspirant substance.

BACKGROUND OF THE INVENTION

In addition to active antiperspirant substances, water-free, antiperspirant suspensions sprayable with a propellant generally contain at least one cosmetic oil as carrier for the particulate active sweat-reducing substance. The suspensions are packaged in a pressure-resistant container, usually a can of tin plate or aluminum, which is lacquered on the inside, together with a liquefied hydrocarbon, such as n-butane, isobutane and/or propane, as propellant. Before using the spray valve, during which propellant and a proportion of the suspension are released, the container must first be shaken sufficiently to mix in the active antiperspirant substance which has settled out. To ensure that the suspended active antiperspirant substance does not immediately settle out again, commercial suspensions contain a suspending agent, for example hydrophobically modified hectorites, as available, for example, with the trade name Bentone Gel from Rheox and Elementis Specialties, or also hydrophilically and/or hydrophobically modified silicas.

In commercial sprays, the active antiperspirant substance suspended in the water-free carrier is covered with an oil layer. During and after application onto the skin, this oil layer is favorable for the spray pattern, in other words the active substance is not excessively atomized, but instead arrives in targeted manner on the skin; the oil layer moreover ensures a certain level of adhesion of the powdered active antiperspirant substance to the skin. However, this oil layer delays the release of the active antiperspirant substance in the effective water-soluble form.

In the prior art, water-containing antiperspirant creams with a water content of 43.9 wt. % are known from U.S. Pat. No. 5,118,497 and U.S. Pat. No. 5,017,360, which are emulsified with the aid of the commercial product Elfacos ST-37, an alkyl-modified polyether with the INCI name PEG-22/Dodecyl Glycol Copolymer, which has an HLB value of 2.4.

U.S. Pat. No. 6,613,338, and in particular WO 98/17238 A1, disclose sticks, in particular antiperspirant sticks, in the form of solid water-in-oil emulsions with a water content of 30-85 wt. %, which are emulsified with the aid of an alkyl-modified polyether of the general formula ACTIVATOR-(I) with the INCI name Methoxy PEG-22/Dodecyl Glycol Copolymer. This prior art gives the person skilled in the art no indication that alkyl-modified polyethers of the general formula ACTIVATOR-(I) might improve the release of the active antiperspirant substance from a water-free composition.

WO 2009/083547 A2 and WO 2009/083807 A2 teach that certain organosiloxane-oxyalkylene copolymers can improve the release of the active antiperspirant substance from a water-free composition. As a disadvantage of these substances, however, it has been shown that under certain circumstances, in particular when the cosmetic carrier contains little or no silicone oil, they are difficult to incorporate and to mix in homogeneously.

Desirable features and characteristics of the present invention will become apparent from the subsequent detailed description of the invention and the appended claims, taken in conjunction with this background of the invention.

BRIEF SUMMARY OF THE INVENTION

Surprisingly, it has now been found that the release of the active antiperspirant substance from a water-free antiperspirant composition can be improved if the composition includes at least one alkyl-modified polyether of the general formula ACTIVATOR-(I)

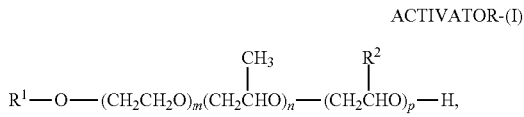

ACTIVATOR-(I)

wherein
  $R^1$ signifies an aliphatic hydrocarbon residue with 1 to 3 C atoms,
  $R^2$ signifies an aliphatic hydrocarbon residue with 8 to 30 C atoms,
  m is a rational number from 10 to 50,
  n is a rational number from 0 to 10,
  p is a rational number from 1 to 10.

The present invention therefore provides antiperspirant compositions for personal body care made up as a suspension or sprayable solution with or without a propellant containing at least one active antiperspirant substance, at least one oil which is liquid under normal conditions as carrier, 0-7 wt. %, preferably 0-3 wt. %, of free water, based on the weight of the propellant-free composition, and at least one alkyl-modified polyether of the general formula ACTIVATOR-(I).

The present invention also is directed to the use of at least one alkyl-modified polyether of the general formula ACTIVATOR-(I) in an antiperspirant composition containing at least one active antiperspirant substance and 0-7 wt. %, preferably 0-3 wt. %, of free water for improving sweat reduction.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The antiperspirant compositions on a water-free basis according to the invention are made up as a suspension or solution which is sprayable without a propellant, for example in a pump dispenser, or with a propellant.

The active antiperspirant substance combination according to the invention is preferably suitable for compositions of a sprayable formulation, in particular for suspensions containing propellant, which are used as an antiperspirant spray.

All of the quantitative data provided below refer, in the case of formulations which are sprayed with a propellant (aerosol sprays), to the weight of the propellant-free composition.

"Normal conditions" within the meaning of the present application are a temperature of 20° C. and a pressure of 1013.25 mbar. Melting point data also refer to a pressure of 1013.25 mbar.

Preferred compositions according to the invention are characterized in that the alkyl-modified polyether d) is selected from compounds of the general formula ACTIVATOR-(I), in which $R^1$ is selected from a methyl group, an ethyl group, an n-propyl group and a 1-methylethyl group, preferably a methyl group, $R^2$ is selected from an n-octyl, 2-ethylhexyl, n-nonyl, n-decyl, 2-ethyloctyl, n-undecyl, n-dodecyl, 2-ethyldecyl, n-tridecyl, myristyl, n-pentadecyl, cetyl, palmityl, stearyl, elaidyl, arachidyl, behenyl or cocyl group, preferably an n-decyl group, m represents a rational number from 12-30, preferably 22-23, n represents a rational number from 0-8, preferably 0-4, particularly preferably 0, p represents a rational number from 1-9, preferably 4-8, particularly preferably 5-7.

Preferred for the teaching according to the invention (composition, use, method) are those alkyl-modified polyethers d) of the general formula ACTIVATOR-(I) in which $R^1$ represents a methyl group.

Also preferred for the teaching according to the invention (composition, use, method) are those alkyl-modified polyethers d) of the general formula ACTIVATOR-(I) in which $R^2$ represents an n-decyl group.

Also preferred for the teaching according to the invention (composition, use, method) are those alkyl-modified polyethers d) of the general formula ACTIVATOR-(I) in which m represents a rational number from 21-23.

Also preferred for the teaching according to the invention (composition, use, method) are those alkyl-modified polyethers d) of the general formula ACTIVATOR-(I) in which m represents a rational number from 22-23.

Also preferred for the teaching according to the invention (composition, use, method) are those alkyl-modified polyethers d) of the general formula ACTIVATOR-(I) in which n=0.

Also preferred for the teaching according to the invention (composition, use, method) are those alkyl-modified polyethers d) of the general formula ACTIVATOR-(I) in which p represents a rational number from 4-5.

Also preferred for the teaching according to the invention (composition, use, method) are those alkyl-modified polyethers d) of the general formula ACTIVATOR-(I) in which p represents a rational number from 6-8.

Also preferred for the teaching according to the invention (composition, use, method) are those alkyl-modified polyethers d) of the general formula ACTIVATOR-(I) in which p represents a rational number from 7-8.

Also preferred for the teaching according to the invention (composition, use, method) are those alkyl-modified polyethers d) of the general formula ACTIVATOR-(I) in which $R^1$ represents a methyl group, $R^2$ an n-decyl group, m a rational number from 22-23, n=0 and p represents a rational number from 4-5.

Also preferred for the teaching according to the invention (composition, use, method) are those alkyl-modified polyethers d) of the general formula ACTIVATOR-(I) in which $R^1$ represents a methyl group, $R^2$ an n-decyl group, m a rational number from 22-23, n=0 and p represents a rational number from 7-8.

Other preferred compositions according to the invention are characterized in that the alkyl-modified polyether d) of the general formula ACTIVATOR-(I), wherein $R^1$ is an aliphatic hydrocarbon residue with 1 to 3 C atoms, $R^2$ is an aliphatic hydrocarbon residue with 8 to 30 C atoms, m is a rational number from 10 to 50, n is a rational number from 0 to 10 and p is a rational number from 1 to 10, has an HLB value in the range of 5-7, preferably 6-6.8, particularly preferably 6.2-6.5.

Other preferred compositions according to the invention are characterized in that the alkyl-modified polyether d) of the general formula ACTIVATOR-(I), wherein $R^1$ is selected from a methyl group, an ethyl group, an n-propyl group and a 1-methylethyl group, preferably a methyl group, $R^2$ is selected from an n-octyl, 2-ethylhexyl, n-nonyl, n-decyl, 2-ethyloctyl, n-undecyl, n-dodecyl, 2-ethyldecyl, n-tridecyl, myristyl, n-pentadecyl, cetyl, palmityl, stearyl, elaidyl, arachidyl, behenyl or cocyl group, preferably an n-decyl group, m represents a rational number from 12-30, preferably 22-23, n represents a rational number from 0-8, preferably 0-4, particularly preferably 0, p represents a rational number from 1-9, preferably 4-8, particularly preferably 5-7, has an HLB value in the range of 5-7, preferably 6-6.8, particularly preferably 6.2-6.5.

Other preferred compositions according to the invention are characterized in that the alkyl-modified polyether d) of the general formula ACTIVATOR-(I) illustrated above, wherein $R^1$ is selected from a methyl group, $R^2$ is selected from an n-decyl group, m is a rational number from 22-23, n=0 and p is a rational number from 4-8, has an HLB value in the range of 5-7, preferably 6-6.8, particularly preferably 6.2-6.5.

Preferred alkyl-modified polyethers of the general formula ACTIVATOR-(I) according to the invention are obtainable by the production method disclosed in U.S. Pat. No. 4,479,887 according to Example 1, in particular Examples 1A and 1D, from a $C_1$-$C_3$ alkanol ethoxylate and a 1,2-epoxy-$C_{10}$-$C_{32}$ alkane. Compositions which are preferred according to the invention are characterized in that the alkyl-modified polyether d) of the general formula ACTIVATOR-(I) is selected from compounds with the INCI name Methoxy PEG-22/Dodecyl Glycol Copolymer. One compound of this type is available, for example, as the commercial product Elfacos E 200.

Other preferred compositions according to the invention are characterized in that at least one alkyl-modified polyether d) of the general formula ACTIVATOR-(I) illustrated above is contained in a total quantity of 0.01-5 wt. %, preferably 0.1-3 wt. %, particularly preferably in a total quantity of 0.5-2 wt. %, extraordinarily preferably in a total quantity of 1-1.5 wt. %, based in each case on the total weight of the propellant-free composition.

Alkyl-modified polyethers d) of the general formula ACTIVATOR-(I) illustrated above can be readily incorporated and homogeneously mixed into the compositions according to the invention, even if the cosmetic carrier contains little or no silicone oil.

The compositions according to the invention are substantially water-free, i.e. they contain 0 to no more than 7 wt. %, preferably 0 to no more than 3 wt. % free water, extraordinarily preferably 0 to no more than 2 wt. %, of free water, based in each case on the overall (propellant-free) composition. The content of water of crystallization, water of hydration or similarly molecularly bound water that can be contained in the components used, in particular in the active antiperspirant substances, does not represent free water within the meaning of the present application.

In a preferred embodiment according to the invention, the active antiperspirant substances and optionally other active substances that are insoluble in the carrier are suspended in at least one oil that is liquid under normal conditions. To improve the application properties, at least one preferably lipophilic thickener is also added to this suspension as a suspending aid. Other preferred compositions according to the invention are therefore characterized in that they contain at least one lipophilic thickener.

Preferred compositions according to the invention are characterized in that the at least one lipophilic thickener is selected from hydrophobically modified clay minerals, pyrogenic silicas, bentone gels, ethylene/propylene/styrene copolymers, butylene/ethylene/styrene copolymers, dextrin esters, silicone elastomers, waxes that are solid under normal conditions and/or glycerol triesters. Among these, hydrophobically modified clay minerals are particularly preferred. The compositions according to the invention contain, in a preferred embodiment, at least one suspending agent or thickener. Particularly suitable thickeners are hydrophobically modified clay minerals, such as montmorillonites, hectorites and bentonites, in particular disteardimonium hectorite and quaternium-18 hectorite. The commercial thickeners provide these hydrophobically modified clay minerals as powders or in the form of a pre-prepared gel in cyclomethicone and, if desired, a gel activator, such as e.g. propylene carbonate, ethanol or water. Other suitable thickeners are pyrogenic silicas, e.g. the commercial products from the Aerosil® range from Degussa.

Preferred hydrophobically modified clay minerals are selected from hydrophobically modified montmorillonites, hydrophobically modified hectorites and hydrophobically modified bentonites, particularly preferably from disteardimonium hectorite, stearalkonium hectorite, quaternium-18 hectorite and quaternium-18 bentonite. The commercial thickeners provide these hydrophobically modified clay minerals as powders or in the form of a gel in an oil component, preferably in cyclomethicone and/or a non-silicone oil component, such as e.g. propylene carbonate. Gel formation takes place by adding small quantities of activators, such as in particular ethanol or propylene carbonate, but also water. Gels of this type are available, for example, with the trade name Bentone® or Thixogel. Compositions which are preferred according to the invention contain at least one activator in a total quantity of 0.1-7 wt. %, preferably 0.3-5 wt. %, extraordinarily preferably 1.6-3 wt. %, based in each case on the total weight of the propellant-free composition according to the invention. Other compositions which are preferred according to the invention contain at least one activator selected from ethanol, propylene carbonate and water and mixtures thereof, in a total quantity of 0.1-3 wt. %, preferably 0.3-1.6 wt. %, based in each case on the total weight of the propellant-free composition according to the invention. Preferred compositions according to the invention are characterized in that they contain at least one hydrophobically modified clay mineral in a total quantity of 0.5-10 wt. %, preferably 1-7 wt. %, particularly preferably 2-6 wt. %, extraordinarily preferably 3-5 wt. %, based in each case on the total weight of the propellant-free composition according to the invention.

Other preferred lipophilic thickeners according to the invention are selected from pyrogenic silicas, e.g. the commercial products from the Aerosil® range from Evonik Degussa. Particularly preferred are hydrophobically modified pyrogenic silicas; Silica Silylate and Silica Dimethyl Silylate are particularly preferred.

Preferred compositions according to the invention are characterized in that they contain at least one pyrogenic silica, preferably at least one hydrophobically modified pyrogenic silica, in a total quantity of 0.5-10 wt. %, preferably 0.8-5 wt. %, particularly preferably 1-4 wt. %, extraordinarily preferably 2-3 wt. %, based in each case on the total weight of the propellant-free composition according to the invention.

Compositions which are preferred according to the invention are characterized in that they contain at least one hydrophilic pyrogenic silica, preferably in a total quantity of 0.1 10 wt. %, particularly preferably 0.3 5 wt. %, preferably 1 2 wt. %, extraordinarily preferably 0.7 1 wt. %, based in each case on the total weight of the propellant-free composition according to the invention. Preferred hydrophilic pyrogenic silicas are available with the trade names Aerosil 200 and Aerosil 300.

Other preferred compositions according to the invention are characterized in that they contain at least one hydrophobically modified pyrogenic silica and at least one hydrophilic silica (INCI: Silica).

Other preferred lipophilic thickeners according to the invention are selected from ethylene/propylene/styrene copolymers and butylene/ethylene/styrene copolymers. The copolymers are particularly preferably used as a pre-thickened oil-based gel.

Preferred compositions according to the invention are characterized in that they contain at least one ethylene/propylene/styrene copolymer and/or butylene/ethylene/styrene copolymer in a total quantity of 0.05-3 wt. %, preferably 0.1-2 wt. %, particularly preferably 0.2-1.0 wt. %, extraordinarily preferably 0.3-0.5 wt. %, based in each case on the total weight of the composition according to the invention.

Other preferred compositions according to the invention are characterized in that they contain at least one silicone rubber. Surprisingly, it has been found that, through the addition of a silicone rubber, the antiperspirant and deodorizing action of the compositions according to the invention can be further prolonged. Without wishing to be bound by this theory, it is assumed that the silicone rubber forms a film on the skin, as a result of which the active antiperspirant substance particles adhere better to the skin.

A particularly preferred silicone rubber according to the invention is selected from silicone polymers with the INCI name Dimethiconol. These dimethiconols are preferably used in a low-concentration solution in cyclomethicone or dimethicone with a kinematic viscosity from 0.65 cSt to no more than 10 cSt. Particularly preferred dimethiconols are available from Dow Corning with the trade names Dow Corning 1401, Dow Corning 1403 and Dow Corning 1501; these products contain 10 to 13 wt. % dimethiconol in cyclomethicone or dimethicone.

Preferred compositions according to the invention are characterized in that they contain at least one silicone rubber in a total quantity of 0.01-1.0 wt. %, preferably 0.05-0.2 wt. %, particularly preferably 0.1-0.15 wt. %, based in each case on the total weight of the composition according to the invention.

The compositions according to the invention contain at least one active antiperspirant substance.

Preferred active antiperspirant substances are selected from the water-soluble astringent inorganic and organic salts of aluminum and zinc or any mixtures of these salts.

Aluminosilicates and zeolites are not included in the active antiperspirant substances according to the invention.

According to the invention, water solubility is understood as a solubility of at least 5 wt. % at 20° C., i.e. quantities of at least 5 g of the active antiperspirant substance are soluble in 95 g water at 20° C.

Particularly preferred active antiperspirant substances are selected from aluminum chlorohydrate, in particular aluminum chlorohydrate with the general formula $[Al_2(OH)_5Cl.1\text{-}6H_2O]_n$, preferably $[Al_2(OH)_5Cl.2\text{-}3H_2O]_n$, which can be present in non-activated or in activated (depolymerized) form, and aluminum chlorohydrate with the general formula $[Al_2(OH)_4Cl_2.1\text{-}6H_2O]_n$, preferably $[Al_2(OH)_4Cl_2.2\text{-}3H_2O]_n$, which can be present in non-activated or in activated (depolymerized) form.

The production of preferred active antiperspirant substances is disclosed, for example, in U.S. Pat. No. 3,887,692, U.S. Pat. No. 3,904,741, U.S. Pat. No. 4,359,456, GB 2048229 and GB 1347950.

Also preferred are aluminum sesquichlorohydrate, aluminum dichlorohydrate, aluminum chlorohydrex-propylene glycol (PG) or aluminum chlorohydrex-polyethylene glycol (PEG), aluminum glycol complexes, e.g. aluminum-propylene glycol complexes, aluminum sesquichlorohydrex-PG or aluminum sesquichlorohydrex-PEG, aluminum-PG dichlorohydrex or aluminum-PEG dichlorohydrex, aluminum hydroxide, also selected from potassium aluminum sulfate ($KAl(SO_4)_2.12H_2O$, alum), aluminum undecylenoyl collagen amino acid, sodium aluminum lactate+aluminum sulfate, sodium aluminum chlorohydroxylactate, aluminum bromohydrate, aluminum chloride, the complexes of zinc and sodium salts, the aluminum salts of lipoamino acids, aluminum sulfate, aluminum lactate, aluminum chlorohydroxyallantoinate, sodium-aluminum chlorohydroxylactate, zinc chloride, zinc sulfocarbolate and zinc sulfate.

Particularly preferred active antiperspirant substances according to the invention are selected from so-called "activated" aluminum salts, which are also referred to as active antiperspirant substances with enhanced activity. These active substances are known in the prior art and are also commercially available. Their production is disclosed, for example, in GB 2048229, U.S. Pat. No. 4,775,528 and U.S. Pat. No. 6,010,688. Activated aluminum salts are generally produced by heat treatment of a relatively dilute solution of the salt (e.g. about 10 wt. % salt), to increase its HPLC peak 4 to peak 3 area ratio. The activated salt can then be dried, in particular spray-dried, to form a powder. In addition to spray drying, roll drying is also suitable, for example.

Activated aluminum salts typically have an HPLC peak 4 to peak 3 area ratio of at least 0.4, preferably at least 0.7, particularly preferably at least 0.9, with at least 70% of the aluminum being assigned to these peaks.

Activated aluminum salts do not necessarily have to be used as a spray-dried powder. Other preferred active antiperspirant substances according to the invention are non-aqueous solutions or solubilizates of an activated antiperspirant aluminum salt, for example according to U.S. Pat. No. 6,010,688, which are stabilized against loss of activation against the rapid degradation of the HPLC peak 4:peak 3 area ratio of the salt by adding an effective quantity of a polyhydric alcohol having 3 to 6 carbon atoms and 3 to 6 hydroxyl groups, preferably propylene glycol, sorbitol and pentaerythritol. For example, compositions are preferred which contain, as percentages by weight (USP):18-45 wt. % of an activated aluminum salt, 55-82 wt. % of at least one anhydrous polyhydric alcohol with 3 to 6 carbon atoms and 3 to 6 hydroxyl groups, preferably propylene glycol, butylene glycol, diethylene glycol, dipropylene glycol, glycerol, sorbitol and pentaerythritol, particularly preferably propylene glycol.

Particularly preferred are also complexes of activated antiperspirant aluminum salts with a polyhydric alcohol which contain 20-50 wt. %, particularly preferably 20-42 wt. %, of activated antiperspirant aluminum salt and 2-16 wt. % of molecularly bound water, the remainder to 100 wt. % being at least one polyhydric alcohol with 3 to 6 carbon atoms and 3 to 6 hydroxyl groups. Propylene glycol, propylene glycol/sorbitol mixtures and propylene glycol/pentaerythritol mixtures are preferred alcohols of this type. Such complexes of an activated antiperspirant aluminum salt with a polyhydric alcohol, which are preferred according to the invention, are disclosed e.g. in U.S. Pat. No. 5,643,558 and U.S. Pat. No. 6,245,325.

Other preferred active antiperspirant substances are basic calcium-aluminum salts, as disclosed for example in U.S. Pat. No. 2,571,030. These salts are produced by reacting calcium carbonate with aluminum chlorhydroxide or aluminum chloride and aluminum powder or by adding calcium chloride dihydrate to aluminum chlorhydroxide.

Other preferred active antiperspirant substances are activated aluminum salts, as disclosed for example in U.S. Pat. No. 6,245,325 or U.S. Pat. No. 6,042,816, containing 5-78 wt. % (USP) of an activated antiperspirant aluminum salt, an amino acid or hydroxyalkanoic acid in such a quantity as to provide an (amino acid or hydroxyalkanoic acid) to aluminum weight ratio of 2:1-1:20 and preferably 1:1 to 1:10, and a water-soluble calcium salt in such a quantity as to provide a Ca:Al weight ratio of 1:1-1:28 and preferably 1:2-1:25.

Particularly preferred solid activated antiperspirant salt compositions, for example according to U.S. Pat. No. 6,245,325 or U.S. Pat. No. 6,042,816, contain 48-78 wt. % (USP), preferably 66-75 wt. %, of an activated aluminum salt and 1-16 wt. %, preferably 4-13 wt. %, of molecularly bound water (water of hydration), and also sufficient water-soluble calcium salt so that the Ca:Al weight ratio is 1:1-1:28, preferably 1:2-1:25, and sufficient amino acid so that the amino acid to (Al+Zr) weight ratio is 2:1-1:20, preferably 1:1-1:10.

Other particularly preferred solid antiperspirant activated salt compositions, for example according to U.S. Pat. No. 6,245,325 or U.S. Pat. No. 6,042,816, contain 48-78 wt. % (USP), preferably 66-75 wt. % of an activated aluminum salt and 1-16 wt. %, preferably 4-13 wt. %, of molecularly bound water (water of hydration), as well as sufficient water-soluble calcium salt so that the Ca:Al weight ratio is 1:1-1:28, preferably 1:2-1:25, and sufficient glycine so that the glycine to Al weight ratio is 2:1-1:20, preferably 1:1-1:10.

Other particularly preferred solid antiperspirant activated salt compositions, for example according to U.S. Pat. No. 6,245,325 or U.S. Pat. No. 6,042,816, contain 48-78 wt. % (USP), preferably 66-75 wt. % of an activated aluminum salt and 1-16 wt. %, preferably 4-13 wt. %, of molecularly bound water, as well as sufficient water-soluble calcium salt so that the Ca:Al weight ratio is 1:1-1:28, preferably 1:2-1:25, and sufficient hydroxyalkanoic acid so that the hydroxyalkanoic acid to Al weight ratio is 2:1-1:20, preferably 1:1-1:10.

Preferred water-soluble calcium salts for stabilizing the antiperspirant salts are selected from calcium chloride, calcium bromide, calcium nitrate, calcium citrate, calcium formate, calcium acetate, calcium gluconate, calcium ascorbate, calcium lactate, calcium glycinate, calcium carbonate, calcium sulfate, calcium hydroxide and mixtures thereof.

Preferred amino acids for stabilizing the antiperspirant salts are selected from glycine, alanine, leucine, isoleucine, β-alanine, valine, cysteine, serine, tryptophan, phenylalanine, methionine, β-amino-n-butanoic acid and γ.amino-n-butanoic acid and the salts thereof, each in the d form, the l form and the dl form; glycine is particularly preferred.

Preferred hydroxyalkanoic acids for stabilizing the antiperspirant salts are selected from glycolic acid and lactic acid.

Other preferred active antiperspirant substances are activated aluminum salts, as disclosed for example in U.S. Pat. No. 6,902,723, containing 5-78 wt. % (USP) of an activated antiperspirant aluminum salt, an amino acid or hydroxyalkanoic acid in a sufficient quantity to provide an (amino acid or hydroxyalkanoic acid) to Al weight ratio of 2:1-1:20 and preferably 1:1 to 1:10, and a water-soluble strontium salt in a sufficient quantity to provide an Sr:Al weight ratio of 1:1-1:28 and preferably 1:2-1:25.

Particularly preferred solid antiperspirant activated salt compositions, for example according to U.S. Pat. No. 6,902,723, contain 48-78 wt. % (USP), preferably 66-'75 wt. %, of an activated aluminum salt and 1-16 wt. %, preferably 4-13 wt. %, of molecularly bound water, as well as sufficient water-soluble strontium salt so that the Sr:Al weight ratio is 1:1-1:28, preferably 1:2-1:25, and sufficient amino acid so that the amino acid to Al weight ratio is 2:1-1:20, preferably 1:1-1:10.

Other particularly preferred solid antiperspirant activated salt compositions, for example according to U.S. Pat. No. 6,902,723, contain 48-78 wt. % (USP), preferably 66-75 wt. %, of an activated aluminum salt and 1-16 wt. %, preferably 4-13 wt. %, of molecularly bound water, as well as sufficient water-soluble strontium salt so that the Sr:Al weight ratio is 1:1-1:28, preferably 1:2-1:25, and sufficient glycine so that the glycine to Al weight ratio is 2:1-1:20, preferably 1:1-1:10.

Other particularly preferred solid antiperspirant activated salt compositions, for example according to U.S. Pat. No. 6,902,723, contain 48-78 wt. % (USP), preferably 66-75 wt. % of an activated aluminum salt and 1-16 wt. %, preferably 4-13 wt. %, of molecularly bound water, as well as sufficient water-soluble strontium salt so that the Sr:Al weight ratio is 1:1-1:28, preferably 1:2-1:25, and sufficient hydroxyalkanoic acid so that the hydroxyalkanoic acid to Al weight ratio is 2:1-1:20, preferably 1:1-1:10.

Other preferred activated aluminum salts are those of the general formula $Al_2(OH)_{6-a}X_a$, wherein X is Cl, Br, I or $NO_3$ and "a" is a value from 0.3 to 5, preferably from 0.8 to 2.5 and particularly preferably 1 to 2, so that the molar ratio of Al:X is 0.9:1 to 2.1:1, as disclosed for example in U.S. Pat. No. 6,074,632. In these salts there is generally some associatively bound water of hydration, typically 1 to 6 moles of water per mole of salt. Particularly preferred is aluminum chlorohydrate (i.e. X is Cl in the aforementioned formula) and especially 5/6-basic aluminum chlorohydrate, wherein "a" is 1, so that the molar ratio of aluminum to chlorine is 1.9:1 to 2.1:1.

Other preferred active antiperspirant substances are disclosed in U.S. Pat. No. 6,663,854 and US 20040009133.

The active antiperspirant substances can be present both in solubilized and also in undissolved, suspended form.

Insofar as the active antiperspirant substances are present in suspension in a carrier that is immiscible with water, it is preferred for reasons of product stability that the active substance particles have a number-average particle size from 0.1-200 μm, preferably 1-50 μm, particularly preferably 3-20 μm and extraordinarily preferably 5-10 μm. Preferred active substance particles have a volume-average particle size from 0.2-220 μm, preferably 3-60 μm, particularly preferably 4-25 μm, further preferably 5-20 μm and extraordinarily preferably 10-15.5 μm.

Preferred aluminum salts have a molar metal to chloride ratio of from 1.9-2.1, or for sesquichlorohydrates from 1.5:1-1.8:1.

The active antiperspirant substances can be used as non-aqueous solutions or as glycolic solubilizates.

Particularly preferred compositions according to the invention are characterized in that the at least one active antiperspirant substance is contained in a quantity of 5-40 wt. %, preferably 10-35 wt. %, particularly preferably 15-28 wt. % and extraordinarily preferably 23-27 wt. %, based on the total weight of the active substance (USP) free from water of crystallization in the overall propellant-free composition.

In a particularly preferred embodiment, the composition contains an astringent aluminum salt, in particular aluminum chlorohydrate, particularly preferably aluminum chlorohydrate with an active substance (USP) which is free from water of crystallization of 72-88 wt. %, based on the raw material as is. Preferred non-activated aluminum chlorohydrates are, for example, marketed in powder form as Micro Dry®, Micro Dry® Ultrafine or Micro Dry®-323 by Summit/Reheis, as Chlorhydrol® (powder) and in activated form as Reach® 101, Reach® 103, Reach® 501 by Reheis/Summit or AACH-7171 by Summit. Under the name Reach® 301, an aluminum sesquichlorohydrate, which is also particularly preferred, is offered by Reheis.

The compositions according to the invention contain at least one oil as carrier fluid.

Preferred antiperspirant compositions according to the invention contain 30-95 wt. %, preferably 40-93 wt. %, particularly preferably 50-90 wt. %, extraordinarily preferably 55-85 wt. %, based in each case on the overall propellant-free composition, of at least one cosmetic oil that is liquid under normal conditions. A total quantity of cosmetic oil that is liquid under normal conditions of 53, 55, 58, 60, 63, 65, 68, 70, 73, 75, 78 or 80 wt. %, based in each case on the overall propellant-free composition, can also be particularly preferred according to the invention, with a total quantity of 53-73 wt. % being particularly preferred.

The cosmetic oils are differentiated into volatile and non-volatile oils. Non-volatile oils are understood to be those oils that have a vapor pressure of less than 2.66 Pa (0.02 mm Hg) at 20° C. and an atmospheric pressure of 1013 hPa. Volatile oils are understood to be those oils that have a vapor pressure of 2.66 Pa-40000 Pa (0.02 mm-300 mm Hg), preferably 12-12000 Pa (0.1-90 mm Hg), particularly preferably 13-8000 Pa, extraordinarily preferably 30-3000 Pa, further preferably 100-400 Pa, at 20° C. and an atmospheric pressure of 1013 hPa.

Preferred cosmetic oils according to the invention are selected from volatile silicone oils, which include e.g. dialkyl and alkylaryl siloxanes, such as for example cyclotetrasiloxane, cyclopentasiloxane, cyclohexasiloxane, dimethyl polysiloxane, low molecular-weight phenyl trimethicone and methyl phenyl polysiloxane, but also hexamethyl disiloxane, octamethyl trisiloxane and decamethyl tetrasiloxane. Particularly preferred are volatile silicone oils, which may be cyclic, such as e.g. octamethyl cyclotetrasiloxane, decamethyl cyclopentasiloxane and dodecamethyl cyclohexasiloxane and mixtures thereof, as are contained e.g. in the commercial products DC 244, 245, 344 and 345 from Dow Corning (vapor pressure at 20° C. approx. 13-15 Pa). Likewise particularly preferred are volatile linear silicone oils with 2-10 siloxane units, in particular hexamethyl disiloxane ($L_2$), octamethyl trisiloxane ($L_3$), decamethyl tetrasiloxane ($L_4$) and any mixtures of two or three of $L_2$, $L_3$ and/or $L_4$, preferably those mixtures as are contained e.g. in the commercial products DC2-1184, Dow Corning 200 (0.65 cSt) and Dow Corning® 200 (1.5 cSt) from Dow Corning Another preferred volatile silicone oil is a low molecular-weight phenyl trimethicone with a vapor pressure at 20° C. of about 2000 Pa, as is obtainable e.g. from GE Bayer Silicones/Momentive with the name Baysilone Fluid PD 5.

Volatile silicone oils are highly suitable carrier oils for preferred antiperspirant compositions according to the invention, since they provide them with a pleasant skin feel and low marking of clothes. Particularly preferred antiperspirant compositions according to the invention are therefore characterized by a content of at least one volatile silicone oil of 10-95 wt. %, preferably 30-80 wt. %, particularly preferably 40-70 wt. %, extraordinarily preferably 50-60 wt. %, based in each case on the overall propellant-free composition.

As well as or instead of the at least one volatile silicone oil, at least one volatile non-silicone oil can also be contained. Preferred volatile non-silicone oils are selected from $C_8$-$C_{16}$ isoparaffins, in particular from isodecane, isoundecane, isododecane, isotridecane, isotetradecane, isopentadecane and isohexadecane, and mixtures thereof. $C_{10}$-$C_{13}$ isoparaffin mixtures are preferred, in particular those with a vapor pressure at 20° C. of about 10-400 Pa, preferably 13-300 Pa. This at least one volatile non-silicone oil is preferably contained in a total quantity of 10-95 wt. %, preferably 20-70 wt. %, particularly preferably 25-50 wt. %, extraordinarily preferably 30-40 wt. %, based in each case on the overall propellant-free composition.

Owing to the dryer skin feel and the more rapid release of active substance, volatile silicone oils, isoparaffins, in particular selected from isodecane, isoundecane, isododecane, isotridecane, isotetradecane, isopentadecane, isohexadecane or isoeicosane, and mixtures of volatile silicone oils and isoparaffins, in particular selected from isododecane, isohexadecane and isoeicosane, are particularly preferred as carrier oil.

Preferred compositions according to the invention are characterized in that the at least one carrier oil b) which is liquid under normal conditions comprises at least one isoparaffin oil, in particular isodecane, isoundecane, isododecane, isotridecane, isotetradecane, isopentadecane, isohexadecane and isoeicosane.

Other preferred compositions according to the invention are characterized in that the carrier oil b) which is liquid under normal conditions comprises a mixture of b)i) a volatile silicone oil, selected from cyclomethicone and linear polydimethyl siloxanes with 2-10 siloxane units, and b)ii) at least one isoparaffin oil, selected from isodecane, isoundecane, isododecane, isotridecane, isotetradecane, isopentadecane, isohexadecane and isoeicosane.

As well as the above-mentioned substances, generally referred to as "volatile" silicone oils, and as well as the aforementioned volatile non-silicone oils, particularly preferred antiperspirant compositions according to the invention can additionally contain at least one non-volatile cosmetic oil, selected from non-volatile silicone oils and non-volatile non-silicone oils. The at least one non-volatile oil compensates for the negative effect of the volatile oil on the residue behavior of preferred antiperspirant compositions according to the invention.

As a result of the relatively rapid evaporation of the volatile oils, solid, insoluble components, in particular the active antiperspirant substances, can become visible on the skin as an unattractive residue. These residues can be successfully masked with a non-volatile oil. In addition, with a mixture of non-volatile and volatile oil, parameters such as skin feel, visibility of the residue and stability of the suspension can be finely regulated and better adapted to the requirements of the consumer.

Preferred non-volatile silicone oils are selected from relatively high molecular weight linear dimethyl polysiloxanes, commercially available e.g. with the name Dow Corning® 190, Dow Corning® 200 Fluid with kinematic viscosities (25° C.) in the range of 5-100 cSt, preferably 6-50 cSt or 5-10 cSt, and Baysilon® 350 M (with a kinematic viscosity (25° C.) of approx. 350 cSt).

Likewise preferred silicone oils according to the invention are selected from silicones of the formula (Sil-1), wherein x is selected from integers from 1-20.

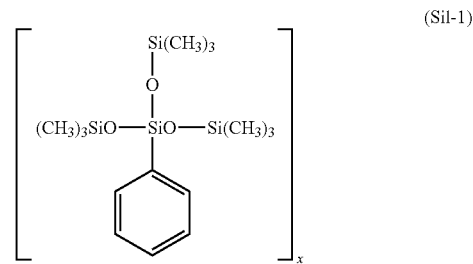

(Sil-1)

A preferred silicone oil of the formula (Sil-1) is available with the INCI name Phenyl Trimethicone in various grades, viscosities and volatilities. A non-volatile Phenyl Trimethicone is available, for example, from Dow Corning with the name Dow Corning 556.

Particularly preferred non-volatile non-silicone oils according to the invention are selected from the esters of linear or branched saturated or non-volatile non-silicone oils unsaturated fatty alcohols having 2-30 carbon atoms with linear or branched saturated or unsaturated fatty acids having 2-30 carbon atoms, which may be hydroxylated. Among these, isopropyl palmitate, isopropyl stearate, isopropyl myristate, 2-ethylhexyl palmitate (Cegesoft® C 24) and 2-ethylhexyl stearate (Cetiol® 868) are extraordinarily preferred. Likewise preferred are hexyldecyl stearate (Eutanol® G16S), hexyldecyl laurate, isononyl isononanoate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid 2-butyloctanoate, diisotridecyl acetate, n-hexyl laurate, n-decyl oleate, oleyl oleate, oleyl erucate, erucyl oleate and erucyl erucate.

Other non-volatile non-silicone oils that are preferred according to the invention are selected from the benzoic acid esters of linear or branched $C_{8-22}$ alkanols. Benzoic acid $C_{12}$-$C_{15}$ alkyl esters, e.g. obtainable as the commercial product Finsolv® TN, isostearyl benzoate, e.g. obtainable as the commercial product Finsolv® SB, ethylhexyl benzoate, e.g. obtainable as the commercial product Finsolv® EB, and octyldodecyl benzoate, e.g. obtainable as the commercial product Finsolv® BOD are particularly preferred, with benzoic acid $C_{12}$-$C_{15}$ alkyl esters being extraordinarily preferred.

Another preferred non-volatile non-silicone oil according to the invention is triethyl citrate.

Other particularly preferred non-volatile non-silicone oils according to the invention are selected from the dicarboxylic acid esters of linear or branched $C_2$-$C_{10}$ alkanols, in particular diisopropyl adipate, di-n-butyl adipate, di-(2-ethylhexyl)adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate and di-(2-hexyldecyl)succinate.

Other particularly preferred non-volatile non-silicone oils according to the invention are selected from the addition products of 1 to 5 propylene oxide units to mono- or polyhydric $C_{8-22}$ alkanols such as octanol, decanol, decanediol, lauryl alcohol, myristyl alcohol and stearyl alcohol, e.g. PPG-2 myristyl ether and PPG-3 myristyl ether (Witconol® APM).

Other particularly preferred non-volatile non-silicone oils according to the invention are selected from the addition products of at least 6 ethylene oxide and/or propylene oxide units to mono- or polyhydric $C_{3-22}$ alkanols such as glycerol, butanol, butanediol, myristyl alcohol and stearyl alcohol, which may be esterified if desired, e.g. PPG-14 butyl ether (Ucon Fluid® AP), PPG-9 butyl ether (Breox® B25), PPG-10 butanediol (Macol® 57), PPG-15 stearyl ether (Arlamol® E) and glycereth-7 diisononanoate.

Natural and synthetic hydrocarbons, such as for example paraffin oils, $C_{18}$-$C_{30}$ isoparaffins, in particular isoeicosane, polyisobutene or polydecene, which are available, for example, with the name Emery® 3004, 3006, 3010 or with the name Ethylflo® from Albemarle or Nexbase® 2004G from Nestle, and 1,3-di-(2-ethylhexyl)cyclohexane (available e.g. with the trade name Cetiol® S from Cognis), also belong to the preferred non-volatile non-silicone oils according to the invention.

Other preferred non-volatile non-silicone oils according to the invention are selected from branched, saturated or unsaturated fatty alcohols with 6-30 carbon atoms. These alcohols are often also referred to as Guerbet alcohols, as they are obtainable by the Guerbet reaction. Preferred alcohol oils are hexyl decanol (Eutanol® G 16), octyl dodecanol (Eutanol® G) and 2-ethylhexyl alcohol.

Other preferred non-volatile non-silicone oils are selected from mixtures of Guerbet alcohols and Guerbet alcohol esters, e.g. the commercial product Cetiol® PGL (hexyl decanol and hexyl decyl laurate).

Other preferred non-volatile non-silicone oils according to the invention are selected from the mono- and polyesters of lactic acid, citric acid, tartaric acid or adipic acid with a di-, tri- or tetrahydric alcohol having 2 to 9 carbon atoms. Particularly preferred esters of this type are selected from ethylene glycol monolactate, ethylene glycol monocitrate, ethylene glycol monotartrate, ethylene glycol monoadipate, ethylene glycol dilactate, ethylene glycol dicitrate, ethylene glycol ditartrate, ethylene glycol diadipate, 1,2-propylene glycol monolactate, 1,2-propylene glycol monocitrate, 1,2-propylene glycol monotartrate, 1,2-propylene glycol monoadipate, 1,2-propylene glycol dilactate, 1,2-propylene glycol dicitrate, 1,2-propylene glycol ditartrate, 1,2-propylene glycol diadipate, 1,3-propylene glycol monolactate, 1,3-propylene glycol monocitrate, 1,3-propylene glycol monotartrate, 1,3-propylene glycol monoadipate, 1,3-propylene glycol dilactate, 1,3-propylene glycol dicitrate, 1,3-propylene glycol ditartrate, 1,3-propylene glycol diadipate, 1,2-butylene glycol monolactate, 1,2-butylene glycol monocitrate, 1,2-butylene glycol monotartrate, 1,2-butylene glycol monoadipate, 1,2-butylene glycol dilactate, 1,2-butylene glycol dicitrate, 1,2-butylene glycol ditartrate, 1,2-butylene glycol diadipate, 1,3-butylene glycol monolactate, 1,3-butylene glycol monocitrate, 1,3-butylene glycol monotartrate, 1,3-butylene glycol monoadipate, 1,3-butylene glycol dilactate, 1,3-butylene glycol dicitrate, 1,3-butylene glycol ditartrate, 1,3-butylene glycol diadipate, 1,4-butylene glycol monolactate, 1,4-butylene glycol monocitrate, 1,4-butylene glycol monotartrate, 1,4-butylene glycol monoadipate, 1,4-butylene glycol dilactate, 1,4-butylene glycol dicitrate, 1,4-butylene glycol ditartrate, 1,4-butylene glycol diadipate, 1,2-pentanediol monolactate, 1,2-pentanediol monocitrate, 1,2-pentanediol monotartrate, 1,2-pentanediol monoadipate, 1,2-pentanediol dilactate, 1,2-pentanediol dicitrate, 1,2-pentanediol ditartrate, 1,2-pentanediol diadipate, 1,3-pentanediol monolactate, 1,3-pentanediol monocitrate, 1,3-pentanediol monotartrate, 1,3-pentanediol monoadipate, 1,3-pentanediol dilactate, 1,3-pentanediol dicitrate, 1,3-pentanediol ditartrate, 1,3-pentanediol diadipate, 1,4-pentanediol monolactate, 1,4-pentanediol monocitrate, 1,4-pentanediol monotartrate, 1,4-pentanediol monoadipate, 1,4-pentanediol dilactate, 1,4-pentanediol dicitrate, 1,4-pentanediol ditartrate, 1,4-pentanediol diadipate, 1,5-pentanediol monolactate, 1,5-pentanediol monocitrate, 1,5-pentanediol monotartrate, 1,5-pentanediol monoadipate, 1,5-pentanediol dilactate, 1,5-pentanediol dicitrate, 1,5-pentanediol ditartrate, 1,5-pentanediol diadipate, 1,2-hexanediol monolactate, 1,2-hexanediol monocitrate, 1,2-hexanediol monotartrate, 1,2-hexanediol monoadipate, 1,2-hexanediol dilactate, 1,2-hexanediol dicitrate, 1,2-hexanediol ditartrate, 1,2-hexanediol diadipate, 1,3-hexanediol monolactate, 1,3-hexanediol monocitrate, 1,3-hexanediol monotartrate, 1,3-hexanediol monoadipate, 1,3-hexanediol dilactate, 1,3-hexanediol dicitrate, 1,3-hexanediol ditartrate, 1,3-hexanediol diadipate, 1,4-hexanediol monolactate, 1,4-hexanediol monocitrate, 1,4-hexanediol monotartrate, 1,4-hexanediol monoadipate, 1,4-hexanediol dilactate, 1,4-hexanediol dicitrate, 1,4-hexanediol ditartrate, 1,4-hexanediol diadipate, 1,5-hexanediol monolactate, 1,5-hexanediol monocitrate, 1,5-hexanediol monotartrate, 1,5-hexanediol monoadipate, 1,5-hexanediol dilactate, 1,5-hexanediol dicitrate, 1,5-hexanediol ditartrate, 1,5-hexanediol diadipate, 1,6-hexanediol monolactate, 1,6-hexanediol monocitrate, 1,6-hexanediol monotartrate, 1,6-hexanediol monoadipate, 1,6-hexanediol dilactate, 1,6-hexanediol dicitrate, 1,6-hexanediol ditartrate, 1,6-hexanediol diadipate, 2-ethylhexane-1,2-diol monolactate, 2-ethylhexane-1,2-diol monocitrate, 2-ethylhexane-1,2-diol monotartrate, 2-ethylhexane-1,2-diol monoadipate, 2-ethylhexane-1,2-diol dilactate, 2-ethylhexane-1,2-diol dicitrate, 2-ethylhexane-1,2-diol ditartrate, 2-ethylhexane-1,2-diol diadipate, 2-ethylhexane-1,3-diol monolactate, 2-ethylhexane-1,3-diol monocitrate, 2-ethylhexane-1,3-diol monotartrate, 2-ethylhexane-1,3-diol monoadipate, 2-ethylhexane-1,3-diol dilactate, 2-ethylhexane-1,3-diol dicitrate, 2-ethylhexane-1,3-diol ditartrate, 2-ethylhexane-1,3-diol diadipate, 2-ethylhexane-1,4-diol monolactate, 2-ethylhexane-1,4-diol monocitrate, 2-ethylhexane-1,4-diol monotartrate, 2-ethylhexane-1,4-diol monoadipate, 2-ethylhexane-1,4-diol dilactate, 2-ethylhexane-1,4-diol dicitrate, 2-ethylhexane-1,4-diol ditartrate, 2-ethylhexane-1,4-diol diadipate, 2-ethylhexane-1,5-diol monolactate, 2-ethylhexane-1,5-diol monocitrate, 2-ethylhexane-1,5-diol monotartrate, 2-ethylhexane-1,5-diol monoadipate, 2-ethylhexane-1,5-diol dilactate, 2-ethylhexane-1,5-diol dicitrate, 2-ethylhexane-1,5-diol ditartrate, 2-ethylhexane-1,5-diol diadipate, 2-ethylhexane-1,6-diol monolactate, 2-ethylhexane-1,6-diol monocitrate, 2-ethylhexane-1,6-diol monotartrate, 2-ethylhexan-1,6-diol monoadipate, 2-ethylhexane-1,6-diol dilactate, 2-ethylhexane-1,6-diol dicitrate, 2-ethylhexane-1,6-diol ditartrate, 2-ethylhexan-1,6-diol diadipate, 1,2-heptanediol monolactate, 1,2-heptanediol monocitrate, 1,2-heptanediol monotartrate, 1,2-heptanediol monoadipate, 1,2-heptanediol dilactate, 1,2-heptanediol dicitrate, 1,2-heptanediol ditartrate, 1,2-heptanediol diadipate, 1,3-heptanediol monolactate, 1,3-heptanediol monocitrate, 1,3-heptanediol monotartrate, 1,3-heptanediol monoadipate, 1,3-heptanediol dilactate, 1,3-heptanediol dicitrate, 1,3-heptanediol ditartrate, 1,3-heptanediol diadipate, 1,4-heptanediol monolactate, 1,4-heptanediol monocitrate, 1,4-heptanediol monotartrate, 1,4-heptanediol monoadipate, 1,4-heptanediol dilactate, 1,4-heptanediol dicitrate, 1,4-heptanediol ditartrate, 1,4- heptanediol diadipate, 1,5-heptanediol monolactate, 1,5-heptanediol monocitrate, 1,5-heptanediol monotartrate, 1,5-heptanediol monoadipate, 1,5-heptanediol dilactate, 1,5-heptanediol dicitrate, 1,5-heptanediol ditartrate, 1,5-heptanediol diadipate, 1,6-heptanediol monolactate, 1,6-heptanediol monocitrate, 1,6-heptanediol monotartrate, 1,6-heptanediol mono adipate, 1,6-heptanediol dilactate, 1,6-heptanediol dicitrate, 1,6-heptanediol ditartrate, 1,6-heptanediol diadipate, 1,7-heptanediol monolactate, 1,7-heptanediol monocitrate, 1,7-heptanediol monotartrate, 1,7-heptanediol monoadipate, 1,7-heptanediol dilactate, 1,7-heptanediol dicitrate, 1,7-heptanediol ditartrate, 1,7-heptanediol diadipate, 1,2-octanediol monolactate, 1,2-octanediol monocitrate, 1,2-octanediol monotartrate, 1,2-octanediol monoadipate, 1,2-octanediol dilactate, 1,2-octanediol dicitrate, 1,2-octanediol ditartrate, 1,2-octanediol diadipate, 1,3-octanediol monolactate, 1,3-octanediol monocitrate, 1,3-octanediol monotartrate, 1,3-octanediol monoadipate, 1,3-octanediol dilactate, 1,3-octanediol dicitrate, 1,3-octanediol ditartrate, 1,3-octanediol diadipate, 1,4-octanediol monolactate, 1,4-octanediol monocitrate, 1,4-octanediol monotartrate, 1,4-octanediol monoadipate, 1,4-octanediol dilactate, 1,4-octanediol dicitrate, 1,4-octanediol ditartrate, 1,4-octanediol diadipate, 1,5-octanediol monolactate, 1,5-octanediol monocitrate, 1,5-octanediol monotartrate, 1,5-octanediol monoadipate, 1,5-octanediol dilactate, 1,5-octanediol dicitrate, 1,5-octanediol ditartrate, 1,5-octanediol diadipate, 1,6-octanediol monolactate, 1,6-octanediol monocitrate, 1,6-octanediol monotartrate, 1,6-octanediol monoadipate, 1,6-octanediol dilactate, 1,6-octanediol dicitrate, 1,6-octanediol ditartrate, 1,6-octanediol diadipate, 1,7-octanediol monolactate, 1,7-octanediol monocitrate, 1,7-octanediol monotartrate, 1,7-octanediol monoadipate, 1,7-octanediol dilactate, 1,7-octanediol dicitrate, 1,7-octanediol ditartrate, 1,7-octanediol diadipate, 1,8-octanediol monolactate, 1,8-octanediol monocitrate, 1,8-octanediol monotartrate, 1,8-octanediol monoadipate, 1,8-octanediol dilactate, 1,8-octanediol dicitrate, 1,8-octanediol ditartrate, 1,8-octanediol diadipate, 2-methyl-1,3-propanediol monolactate, 2-methyl-1,3-propanediol monocitrate, 2-methyl-1,3-propanediol monotartrate, 2-methyl-1,3-propanediol monoadipate, 2-methyl-1,3-propanediol dilactate, 2-methyl-1,3-propanediol dicitrate, 2-methyl-1,3-propanediol ditartrate, 2-methyl-1,3-propanediol diadipate, dipropylene glycol monolactate, dipropylene glycol monotartrate, dipropylene glycol monocitrate, dipropylene glycol monoadipate, dipropylene glycol dilactate, dipropylene glycol ditartrate, dipropylene glycol dicitrate, dipropylene glycol diadipate, glycerol monolactate, glycerol monotartrate, glycerol monocitrate, glycerol monoadipate, glycerol dilactate, glycerol ditartrate, glycerol dicitrate, glycerol diadipate, glycerol trilactate, glycerol tritartrate, glycerol tricitrate, glycerol triadipate, diglycerol monolactate, diglycerol monotartrate, diglycerol monocitrate, diglycerol monoadipate, diglycerol dilactate, diglycerol ditartrate, diglycerol dicitrate, diglycerol diadipate, diglycerol trilactate, diglycerol tritartrate, diglycerol tricitrate, diglycerol triadipate, tripropylene glycol monolactate, tripropylene glycol monotartrate, tripropylene glycol monocitrate, tripropylene glycol monoadipate, tripropylene glycol dilactate, tripropylene glycol ditartrate, tripropylene glycol dicitrate, tripropylene glycol diadipate, tripropylene glycol trilactate, tripropylene glycol tritartrate, tripropylene glycol tricitrate, tripropylene glycol triadipate, triglycerol monolactate, triglycerol monotartrate, triglycerol monocitrate, triglycerol monoadipate, triglycerol dilactate, triglycerol ditartrate, triglycerol dicitrate, triglycerol diadipate, triglycerol trilactate, triglycerol tritartrate, triglycerol tricitrate, triglycerol triadipate, 1,2,6-hexanetriol monolactate, 1,2,6-hexanetriol monotartrate, 1,2,6-hexanetriol monocitrate, 1,2,6-hexanetriol monoadipate, 1,2,6-hexanetriol dilactate, 1,2,6-hexanetriol ditartrate, 1,2,6-hexanetriol dicitrate, 1,2,6-hexanetriol diadipate, 1,2,6-hexanetriol trilactate, 1,2,6-hexanetriol tritartrate, 1,2,6-hexanetriol tricitrate, 1,2,6-hexanetriol triadipate, trimethylolpropane monolactate, trimethylolpropane monotartrate, trimethylolpropane monocitrate, trimethylolpropane monoadipate, trimethylolpropane dilactate, trimethylolpropane ditartrate, trimethylolpropane dicitrate, trimethylolpropane diadipate, trimethylolpropane trilactate, trimethylolpropane tritartrate, trimethylolpropane tricitrate, trimethylolpropane triadipate, trimethylolethane monolactate, trimethylolethane monotartrate, trimethylolethane monocitrate, trimethylolethane monoadipate, trimethylolethane dilactate, trimethylolethane ditartrate, trimethylolethane dicitrate, trimethylolethane diadipate, trimethylolethane trilactate, trimethylolethane tritartrate, trimethylolethane tricitrate and trimethylolethane triadipate, and mixtures thereof.

Other preferred non-volatile non-silicone oils according to the invention are selected from the triglycerides of linear or branched, saturated or unsaturated, optionally hydroxylated $C_{8-30}$ fatty acids. The use of natural oils can be particularly suitable, e.g. soybean oil, cottonseed oil, sunflower oil, palm oil, palm kernel oil, linseed oil, almond oil, castor oil, corn oil, rapeseed oil, olive oil, sesame oil, thistle oil, wheat germ oil, peach stone oil and the liquid fractions of coconut oil and the like. However, synthetic triglyceride oils are also suitable, in particular capric/caprylic triglycerides, e.g. the commercial products Myritol® 318, Myritol® 331 (Cognis) or Miglyol® 812 (Hüls) with unbranched fatty acid residues and glyceryl triisostearin with branched fatty acid residues.

Other particularly preferred non-volatile non-silicone oils according to the invention are selected from the symmetrical, asymmetrical or cyclic esters of carbonic acid with fatty alcohols, e.g. glycerol carbonate, dicaprylyl carbonate (Cetiol® CC), di-n-octyl carbonate, di-n-dodecyl carbonate, di(2-ethylhexyl)carbonate or the esters according to the teaching of DE 19756454 A. Other oils that may be preferred according to the invention are selected from the esters of dimers of unsaturated $C_{12}$-$C_{22}$ fatty acids (dimer fatty acids) with monohydric linear, branched or cyclic $C_2$-$C_{18}$ alkanols or with polyhydric linear or branched $C_2$-$C_6$ alkanols.

It may be preferred according to the invention to use mixtures of the aforementioned oils.

Other preferred compositions according to the invention are characterized in that at least one non-volatile non-silicone oil is contained in a total quantity of 10-95 wt. %, preferably 15-75 wt. %, particularly preferably 18-50 wt. %, extraordinarily preferably 20-35 wt. %, based in each case on the overall propellant-free composition.

Cyclomethicone-Reduced Carriers

According to another, also preferred embodiment, the water-free antiperspirant compositions according to the invention contain a small proportion of no more than 2 wt. %, preferably no more than 1 wt. %, of cyclomethicone or are even free from cyclomethicone. As a substitute for cyclomethicone, the $C_8$-$C_{16}$ isoparaffins, in particular selected from isononane, isodecane, isoundecane, isododecane, isotridecane, isotetradecane, isopentadecane and isohexadecane, and mixtures thereof, are particularly preferred. $C_{10}$-$C_{13}$ isoparaffin mixtures are preferred, in particular those with a vapor pressure at 20° C. of about 8-400 Pa, preferably 13-300 Pa.

Cyclomethicone-Reduced Isoparaffin Mixtures

In addition to the at least one aforementioned $C_8$-$C_{16}$ isoparaffin, other preferred antiperspirant compositions according to the invention contain, as well as 0 to no more than 2 wt. %, preferably no more than 1 wt. %, of cyclomethicone, at least one non-volatile cosmetic oil, selected from non-volatile silicone oils and non-volatile non-silicone oils. The at least one non-volatile oil compensates for the negative effect of the volatile isoparaffins on the residue behavior of preferred antiperspirant compositions according to the invention. As a result of the relatively rapid evaporation of the volatile oils, solid, insoluble components, in particular the active antiperspirant substances, can become visible on the skin as an unattractive residue. These residues can be successfully masked with a non-volatile oil. In addition, with a mixture of non-volatile and volatile oil, parameters such as skin feel, visibility of the residue and stability of the suspension can be finely regulated and better adapted to the requirements of the consumer. Particularly preferred non-volatile oils for this purpose are, in particular, the ester oils 2-ethylhexyl palmitate (e.g. Cegesoft® C 24), hexyldecyl laurate, 2-ethylhexyl stearate, isopropyl myristate, isopropyl palmitate and 2-ethylhexyl laurate, the benzoic acid esters of linear or branched $C_{8-22}$ alkanols, in particular the commercial product Finsolv® TN ($C_{12}$-$C_{15}$ alkyl benzoate), $C_{12}$-$C_{15}$ alkyl lactate and di-$C_{12}$-$C_{13}$ alkyl malate are suitable. It can also be particularly preferred to formulate water-free antiperspirant compositions according to the invention without cyclomethicone and without volatile linear silicone oils. For this purpose too, the esters oils 2-ethylhexyl palmitate (e.g. Cegesoft® C 24), hexyldecyl laurate, 2-ethylhexyl stearate, isopropyl myristate, isopropyl palmitate and 2-ethylhexyl laurate, the benzoic acid esters of linear or branched $C_{8-22}$ alkanols, in particular the commercial product Finsolv® TN ($C_{12}$-$C_{15}$ alkyl benzoate), $C_{12}$-$C_{15}$ alkyl lactate and di-$C_{12}$-$C_{13}$ alkyl malate are particularly preferably suitable.

Particularly preferred oil mixtures according to the invention with 0 to no more than 2 wt. %, preferably 0 to no more than 1 wt. %, of cyclomethicone are 2-ethylhexyl palmitate/isodecane/isoundecane/isododecane/isotridecane, hexyldecyl laurate/isodecane/isoundecane/isododecane/isotridecane, 2-ethylhexyl stearate/isodecane/isoundecane/isododecane/isotridecane, isopropyl myristate/isodecane/isoundecane/isododecane/isotridecane, isopropyl palmitate/isononane/isodecane/isoundecane/isododecane/isotridecane, 2-ethylhexyl laurate/isodecane/isoundecane/isododecane/isotridecane, $C_{12}$-$C_{15}$ alkyl lactate/isodecane/isoundecane/isododecane/isotridecane, $C_{12}$-$C_{15}$ alkyl benzoate/isodecane/isoundecane/isododecane/isotridecane and di-$C_{12}$-$C_{13}$ alkyl malate/isodecane/isoundecane/isododecane/isotridecane.

In preferred oil mixtures with 0 to no more than 2 wt. %, preferably 0 to no more than 1 wt. %, of cyclomethicone, the two types of oil (esters/$C_8$-$C_{16}$ isoparaffin) are contained in approximately equal proportions by weight, i.e. in weight ratios of esters/$C_8$-$C_{16}$ isoparaffin of 0.9 to 1.2, preferably 1 to 1.1.

In other preferred embodiments of the invention, there is an excess of $C_8$-$C_{16}$ isoparaffin compared with the ester(s). In these cases, the weight ratio of esters/$C_{8-16}$ isoparaffin is preferably 0.1 to 0.8, particularly preferably 0.3 to 0.6, and extraordinarily preferably 0.4 to 0.5.

In other preferred oil mixtures with 0 to no more than 2 wt. %, preferably 0 to no more than 1 wt. %, of cyclomethicone, the two types of oil, isopropyl myristate/$C_8$-$C_{16}$ isoparaffin, are contained in approximately equal proportions by weight, i.e. in weight ratios of ester/$C_8$-$C_{16}$ isoparaffin of 0.9 to 1.2, preferably 1 to 1.1. Other preferred weight ratios of isopropyl myristate/$C_{8-16}$ isoparaffin are in the range from 0.1 to 0.8, particularly preferably 0.3 to 0.6, extraordinarily preferably 0.4 to 0.5.

In other preferred oil mixtures with 0 to no more than 2 wt. %, preferably 0 to no more than 1 wt. %, of cyclomethicone, the two types of oil, isopropyl palmitate/$C_8$-$C_{16}$ isoparaffin, are contained in approximately equal proportions by weight, i.e. in weight ratios of ester/$C_8$-$C_{16}$ isoparaffin of 0.9 to 1.2, preferably 1 to 1.1. Other preferred weight ratios of isopropyl palmitate/$C_{8-16}$ isoparaffin are in the range from 0.1 to 0.8, particularly preferably 0.3 to 0.6, extraordinarily preferably 0.4 to 0.5.

In other preferred oil mixtures with 0 to no more than 2 wt. %, preferably 0 to no more than 1 wt. %, of cyclomethicone, the two types of oil, 2-ethylhexyl palmitate/$C_8$-$C_{16}$ isoparaffin, are contained in approximately equal proportions by weight, i.e. in weight ratios of ester/$C_8$-$C_{16}$ isoparaffin of 0.9 to 1.2, preferably 1 to 1.1. Other preferred weight ratios of 2-ethylhexyl palmitate/$C_{8-16}$ isoparaffin are in the range from 0.1 to 0.8, particularly preferably 0.3 to 0.6, extraordinarily preferably 0.4 to 0.5.

In other preferred oil mixtures with 0 to no more than 2 wt. %, preferably 0 to no more than 1 wt. %, of cyclomethicone, the two types of oil, $C_{12}$-$C_{15}$ alkyl benzoate/$C_8$-$C_{16}$ isoparaffin, are contained in approximately equal proportions by weight, i.e. in weight ratios of esters/$C_8$-$C_{16}$ isoparaffin of 0.9 to 1.2, preferably 1 to 1.1. Other preferred weight ratios of $C_{12}$-$C_{15}$ alkyl benzoate/$C_{8-16}$ isoparaffin are in the range from 0.1 to 0.8, particularly preferably 0.3 to 0.6, extraordinarily preferably 0.4 to 0.5.

In other preferred oil mixtures with 0 to no more than 2 wt. %, preferably 0 to no more than 1 wt. %, of cyclomethicone, the two types of oil, esters/$C_{10}$-$C_{13}$ isoparaffin, are contained in approximately equal proportions by weight, i.e. in weight ratios of esters/$C_{10}$-$C_{13}$ isoparaffin of 0.9 to 1.2, preferably 1 to 1.1. Other preferred weight ratios of esters/$C_{10-13}$ isoparaffin are in the range from 0.1 to 0.8, particularly preferably 0.3 to 0.6, extraordinarily preferably 0.4 to 0.5.

In other preferred oil mixtures with 0 to no more than 2 wt. %, preferably 0 to no more than 1 wt. %, of cyclomethicone, the two types of oil, isopropyl myristate/$C_{10}$-$C_{13}$ isoparaffin, are contained in approximately equal proportions by weight, i.e. in weight ratios of ester/$C_{10}$-$C_{13}$ isoparaffin of 0.9 to 1.2, preferably 1 to 1.1. Other preferred weight ratios of isopropyl myristate/$C_{10-13}$ isoparaffin are in the range from 0.1 to 0.8, particularly preferably 0.3 to 0.6, extraordinarily preferably 0.4 to 0.5.

In other preferred oil mixtures with 0 to no more than 2 wt. %, preferably 0 to no more than 1 wt. %, of cyclomethicone, the two types of oil, isopropyl palmitate/$C_{10}$-$C_{13}$ isoparaffin, are contained in approximately equal proportions by weight, i.e. in weight ratios of ester/$C_{10}$-$C_{13}$ isoparaffin of 0.9 to 1.2, preferably 1 to 1.1. Other preferred weight ratios of isopropyl palmitate/$C_{10-13}$ isoparaffin are in the range from 0.1 to 0.8, particularly preferably 0.3 to 0.6, extraordinarily preferably 0.4 to 0.5.

In other preferred oil mixtures with 0 to no more than 2 wt. %, preferably 0 to no more than 1 wt. %, of cyclomethicone, the two types of oil, 2-ethylhexyl palmitate/$C_{10}$-$C_{13}$ isoparaffin, are contained in approximately equal proportions by weight, i.e. in weight ratios of ester/$C_{10}$-$C_{13}$ isoparaffin of 0.9 to 1.2, preferably 1 to 1.1. Other preferred weight ratios of 2-ethylhexyl palmitate/$C_{10-13}$ isoparaffin are in the range from 0.1 to 0.8, particularly preferably 0.3 to 0.6, extraordinarily preferably 0.4 to 0.5.

In other preferred oil mixtures with 0 to no more than 2 wt. %, preferably 0 to no more than 1 wt. %, of cyclomethicone, the two types of oil, $C_{12}$-$C_{15}$ alkyl benzoate/$C_{10}$-$C_{13}$ isoparaffin, are contained in approximately equal proportions by weight, i.e. in weight ratios of esters/$C_{10}$-$C_{13}$ isoparaffin of 0.9 to 1.2, preferably 1 to 1.1. Other preferred weight ratios of $C_{12}$-$C_{15}$ alkyl benzoate/$C_{10-13}$ isoparaffin are in the range from 0.1 to 0.8, particularly preferably 0.3 to 0.6, extraordinarily preferably 0.4 to 0.5.

Particularly preferred compositions according to the invention are characterized in that the carrier oil b) which is liquid under normal conditions comprises a mixture b)i)+b)ii)+b)iii) of b)i) an ester oil selected from 2-ethylhexyl palmitate, isopropyl myristate and isopropyl palmitate, and b)ii) at least one isoparaffin oil, selected from isodecane, isoundecane, isododecane, isotridecane, isotetradecane, isopentadecane, isohexadecane and isoeicosane, and b)iii) 0—no more than 1 wt. % cyclomethicone.

Other particularly preferred compositions according to the invention are characterized in that the carrier oil b) which is liquid under normal conditions consists of a mixture b)i)+b)ii)+b)iii) of b)i) an ester oil, selected from 2-ethylhexyl palmitate, isopropyl myristate and isopropyl palmitate, and b)ii) at least one isoparaffin oil, selected from isodecane, isoundecane, isododecane, isotridecane, isotetradecane, isopentadecane, isohexadecane and isoeicosane, and b)iii) 0 to no more than 1 wt. % cyclomethicone.

Oil Mixtures Comprising Triethyl Citrate

Other preferred compositions according to the invention are characterized in that the carrier oil which is liquid under normal conditions is selected from a mixture of triethyl citrate and at least one other cosmetic oil which is liquid under normal conditions as carrier, wherein the proportion by weight of triethyl citrate in the total quantity of oils, based on the overall propellant-free composition, is 13-50 wt. % and 0 to less than 1 wt. % of cyclomethicone, based on the weight of the propellant-free composition, is contained. The proportion by weight of triethyl citrate in the total oil content is preferably 12-40 wt. %, particularly preferably 16-35 wt. %, extraordinarily preferably 20-30 wt. %. The propellant should not be taken into account when determining total oil content.

Particularly preferred oil mixtures according to the invention are triethyl citrate/2-ethylhexyl palmitate/isodecane/isoundecane/isododecane/isotridecane, triethyl citrate/hexyldecyl laurate/isodecane/isoundecane/isododecane/isotridecane, triethyl citrate/2-ethylhexyl stearate/isodecane/isoundecane/isododecane/isotridecane, triethyl citrate/isopropyl myristate/isodecane/isoundecane/isododecane/isotridecane, triethyl citrate/isopropyl palmitate/isononane/isodecane/isoundecane/isododecane/isotridecane, triethyl citrate/2-ethylhexyl laurate/isodecane/isoundecane/isododecane/isotridecane, triethyl citrate/$C_{12}$-$C_{15}$ alkyl lactate/isodecane/isoundecane/isododecane/isotridecane, triethyl citrate/$C_{12}$-$C_{15}$ alkyl benzoate/isodecane/isoundecane/isododecane/isotridecane and triethyl citrate/di-$C_{12}$-$C_{13}$ alkyl malate/isodecane/isoundecane/isododecane/isotridecane.

In preferred oil mixtures, all three types of oil (triethyl citrate/ester/$C_8$-$C_{16}$ isoparaffin) are contained in equal proportions by weight. Other preferred weight ratios of triethyl citrate/ester/$C_{8-16}$ isoparaffin are (1-1.3):(0.6-1):(1-3). Other preferred weight ratios of triethyl citrate/ester/$C_8$-$C_{16}$ isoparaffin are (1-1.3):1:(1-1.5). Other preferred weight ratios of triethyl citrate/esters/$C_8$-$C_{16}$ isoparaffin are (1-1.3):(0.6-0.9):(2.5-3), in particular 1:0.8:3.

In preferred oil mixtures, all three types of oil (triethyl citrate/isopropyl myristate/$C_8$-$C_{16}$ isoparaffin) are contained in equal proportions by weight. Other preferred weight ratios of triethyl citrate/isopropyl myristate/$C_{8-16}$ isoparaffin are (1-1.3):(0.6-1):(1-3). Other preferred weight ratios of triethyl citrate/isopropyl myristate/$C_8$-$C_{16}$ isoparaffin are (1-1.3):1:(1-1.5). Other preferred weight ratios of triethyl citrate/isopropyl myristate/$C_8$-$C_{16}$ isoparaffin are (1-1.3):(0.6-0.9):(2.5-3), in particular 1:0.8:3.

In preferred oil mixtures, all three types of oil (triethyl citrate/isopropyl palmitate/$C_8$-$C_{16}$ isoparaffin) are contained in equal proportions by weight. Other preferred weight ratios of triethyl citrate/isopropyl palmitate/$C_{8-16}$ isoparaffin are (1-1.3):(0.6-1):(1-3). Other preferred weight ratios of triethyl citrate/isopropyl palmitate/$C_8$-$C_{16}$ isoparaffin are (1-1.3):1:(1-1.5). Other preferred weight ratios of triethyl citrate/isopropyl palmitate/$C_8$-$C_{16}$ isoparaffin are (1-1.3):(0.6-0.9):(2.5-3), in particular 1:0.8:3.

In preferred oil mixtures, all three types of oil (triethyl citrate/$C_{12}$-$C_{15}$alkyl benzoate/$C_8$-$C_{16}$ isoparaffin) are contained in equal proportions by weight. Other preferred weight ratios of triethyl citrate/$C_{12}$-$C_{15}$ alkyl benzoate/$C_{8-16}$ isoparaffin are (1-1.3):(0.6-1):(1-3). Other preferred weight ratios of triethyl citrate/$C_{12}$-$C_{15}$ alkyl benzoate/$C_8$-$C_{16}$ isoparaffin are (1-1.3):1:(1-1.5). Other preferred weight ratios of triethyl citrate/$C_{12}$-$C_{15}$alkyl benzoate/$C_8$-$C_{16}$ isoparaffin are (1-1.3):(0.6-0.9):(2.5-3), in particular 1:0.8:3.

In other preferred oil mixtures, all three types of oil (triethyl citrate/ester/$C_{10}$-$C_{13}$ isoparaffin) are contained in equal proportions by weight. Other preferred weight ratios of triethyl citrate/ester/$C_{10-13}$ isoparaffin are (1-1.3):(0.6-1):(1-3). Other preferred weight ratios of triethyl citrate/ester/$C_{10}$-$C_{13}$ isoparaffin are (1-1.3):1:(1-1.5). Other preferred weight ratios of triethyl citrate/ester/$C_{10}$-$C_{13}$ isoparaffin are (1-1.3):(0.6-0.9):(2.5-3), in particular 1:0.8:3.

In preferred oil mixtures, all three types of oil (triethyl citrate/isopropyl myristate/$C_{10}$-$C_{13}$ isoparaffin) are contained in equal proportions by weight. Other preferred weight ratios of triethyl citrate/isopropyl myristate/$C_{10-13}$ isoparaffin are (1-1.3):(0.6-1):(1-3). Other preferred weight ratios of triethyl citrate/isopropyl myristate/$C_{10}$-$C_{13}$ isoparaffin are (1-1.3): 1:(1-1.5). Other preferred weight ratios of triethyl citrate/isopropyl myristate/$C_{10}$-$C_{13}$ isoparaffin are (1-1.3): (0.6-0.9):(2.5-3), in particular 1:0.8:3.

In preferred oil mixtures, all three types of oil (triethyl citrate/isopropyl palmitate/$C_{10}$-$C_{13}$ isoparaffin) are contained in equal proportions by weight. Other preferred weight ratios of triethyl citrate/isopropyl palmitate/$C_{10-13}$ isoparaffin are (1-1.3):(0.6-1):(1-3). Other preferred weight ratios of triethyl citrate/isopropyl palmitate/$C_{10}$-$C_{13}$ isoparaffin are (1-1.3):1:(1-1.5). Other preferred weight ratios of triethyl citrate/isopropyl palmitate/$C_{10}$-$C_{13}$ isoparaffin are (1-1.3): (0.6-0.9):(2.5-3), in particular 1:0.8:3.

In preferred oil mixtures, all three types of oil (triethyl citrate/$C_{12}$-$C_{15}$ alkyl benzoate/$C_{10}$-$C_{13}$ isoparaffin) are contained in equal proportions by weight. Other preferred weight ratios of triethyl citrate/$C_{12}$-$C_{15}$ alkyl benzoate/$C_{10-13}$ isoparaffin are (1-1.3):(0.6-1):(1-3). Other preferred weight ratios of triethyl citrate/$C_{12}$-$C_{15}$ alkyl benzoate/$C_{10}$-$C_{13}$ isoparaffin are (1-1.3):1:(1-1.5). Other preferred weight ratios of triethyl citrate/$C_{12}$-$C_{15}$ alkyl benzoate/$C_{10}$-$C_{13}$ isoparaffin are (1-1.3):(0.6-0.9):(2.5-3), in particular 1:0.8:3.

It may be extraordinarily preferred according to the invention to use mixtures of the aforementioned oils in order to achieve optimum fine adjustment of the product properties, in particular of the residue behavior, the skin feel or the active substance release.

Fragrances and perfumes are not included according to the invention in the cosmetic oils that are taken into account when calculating the proportion by weight of the carrier oils b) described above. Examples of fragrance and perfume compounds of the esters type are benzyl acetate, phenoxyethyl isobutyrate, p-tert.-butyl cyclohexyl acetate, linalyl acetate, dimethyl benzyl carbinyl acetate (DMBCA), phenyl ethyl acetate, benzyl acetate, ethyl methyl phenyl glycinate, allyl cyclohexyl propionate, styrallyl propionate, benzyl salicylate, cyclohexyl salicylate, Floramat, Melusat and Jasmecyclat. Examples of fragrance and perfume compounds of the ethers type are benzyl ethyl ether and Ambroxan; examples of fragrance and perfume compounds of the aldehydes type are the linear alkanals with 8-18 C atoms, citral, citronellal, citronellyl oxyacetaldehyde, cyclamen aldehyde, lilial and bourgeonal; examples of fragrance and perfume compounds of the ketones type are the ionones, alpha-isomethyl ionone and methyl cedryl ketone; examples of fragrance and perfume compounds of the alcohols type are anethole, citronellol, eugenol, geraniol, linalool, phenyl ethyl alcohol and terpineol; examples of fragrance and perfume compounds of the terpenes type are limonene and pinene. Examples of fragrance and perfume compounds are pine oil, citrus oil, jasmine oil, patchouli oil, rose oil, ylang-ylang oil, clary sage oil, chamomile oil, clove oil, mint oil, cinnamon leaf oil, lime blossom oil, juniper berry oil, vetiver oil, olibanum oil, galbanum oil, labdanum oil, orange blossom oil, neroli oil, orange-peel oil and sandalwood oil, as well as the essential oils such as angelica root oil, anise oil, arnica blossom oil, basil oil, bay oil, bergamot oil, champaca flower oil, silver fir oil, silver fir cone oil, elemi oil, eucalyptus oil, fennel oil, fir needle oil, geranium oil, gingergrass oil, guaiacum oil, gurjun balsam oil, helichrysum oil, ho oil, ginger oil, iris oil, cajeput oil, calamus oil, chamomile oil, camphor oil, canaga oil, cardamom oil, cassia oil, pine-needle oil, copaiva balsam oil, coriander oil, curled mint oil, caraway oil, cumin oil, lavender oil, lemongrass oil, lime oil, mandarin oil, melissa oil, musk seed oil, myrrh oil, clove oil, niaouli oil, orange oil, oregano oil, palmarosa oil, patchouli oil, Peru balsam oil, petitgrain oil, pepper oil, peppermint oil, pimento oil, pine oil, rose oil, rosemary oil, sandalwood oil, celery oil, spike oil, star anise oil, turpentine oil, thuja oil, thyme oil, verbena oil, juniper berry oil, wormwood oil, wintergreen oil, hyssop oil, cinnamon oil, citronella oil, lemon oil and cypress oil. Other fragrance and perfume compounds are ambrettolide, α-amyl cinnamaldehyde, anethole, anisaldehyde, anisyl alcohol, anisole, methyl anthranilate, acetophenone, benzyl acetone, benzaldehyde, ethyl benzoate, benzophenone, benzyl alcohol, benzyl acetate, benzyl benzoate, benzyl formate, benzyl valerianate, borneol, bornyl acetate, α-bromostyrene, n-decyl aldehyde, n-dodecyl aldehyde, eugenol, eugenol methyl ether, eucalyptol, farnesol, fenchone, fenchyl acetate, geranyl acetate, geranyl formate, heliotropin, heptyne carboxylic acid methyl ester, heptaldehyde, hydroquinone dimethyl ether, hydroxycinnamaldehyde, hydroxycinnamyl alcohol, indole, irone, isoeugenol, isoeugenol methyl ether, isosafrole, jasmone, camphor, carvacrol, carvone, p-cresol methyl ether, coumarin, p-methoxyacetophenone, methyl n-amyl ketone, methyl anthranilic acid methyl ester, p-methyl acetophenone, methyl chavicol, p-methyl quinoline, methyl β-naphthyl ketone, methyl n-nonyl acetaldehyde, methyl n-nonyl ketone, muscone, β-naphthol ethyl ether, β-naphthol methyl ether, nerol, nitrobenzene, n-nonyl aldehyde, nonyl alcohol, n-octyl aldehyde, p-oxyacetophenone, pentadecanolide, β-phenyl ethyl alcohol, phenyl acetaldehyde dimethyl acetal, phenylacetic acid, pulegone, safrole, isoamyl salicylate, methyl salicylate, hexyl salicylate, cyclohexyl salicylate, santalol, skatole, terpineol, thymene, thymol, γ-undecalactone, vanillin, veratrum aldehyde, cinnamaldehyde, cinnamyl alcohol, cinnamic acid, ethyl cinnamate and benzyl cinnamate.

Other (more readily volatile) perfumes are alkyl isothiocyanates (alkyl mustard oils), butanedione, limonene, linalool, linalyl acetate and propionate, menthol, menthone, methyl n-heptenone, phellandrene, phenyl acetaldehyde, terpinyl acetate, citral and citronellal.

Mixtures of various fragrances are preferably used which together produce an attractive fragrance note.

Suitable perfume oils can also contain natural perfume mixtures as can be obtained from plant or animal sources, e.g. pine, citrus, jasmine, rose, lily or ylang-ylang oils. Essential oils with low volatility, which are mainly used as aroma components, are also suitable as perfume oils, e.g. sage oil, chamomile oil, melissa oil, mint oil, cinnamon leaf oil, limeblossom oil, juniper berry oil, vetiver oil, olibanum oil, galbanum oil, laudanum oil, clove oil, isoeugenol, thyme oil, bergamot oil, geranium oil and rose oil.

Preferred compositions according to the invention are characterized in that at least one fragrance is contained in a total quantity of 0.1-15 wt. %, preferably 0.5-10 wt. %, particularly preferably 1-8 wt. %, extraordinarily preferably 2-7 wt. %, further extraordinarily preferably 3-6 wt. %, based in each case on the total weight of the propellant-free composition.

Other preferred compositions according to the invention are characterized by a content of at least one so-called "skin-cooling active substance". Skin-cooling active substances within the meaning of the present application are understood to be active substances which, when applied onto the skin, as a result of surface anaesthetizing and irritation of the cold-sensitive nerves in migraine and the like, produce a pleasant cool sensation, even if the areas of skin being treated actually display a normal or elevated temperature.

Preferred skin-cooling active substances are, in particular, menthol, isopulegol and menthol derivatives, e.g. menthyl lactate, menthyl pyrrolidone carboxylic acid, menthyl methyl ether, menthoxypropanediol, menthone glycerin acetal (9-methyl-6-(1-methylethyl)-1,4-dioxaspiro(4.5)decane-2-methanol), monomenthyl succinate and 2-hydroxymethyl-3,5,5-trimethyl cyclohexanol. Menthol, isopulegol, menthyl lactate, menthoxypropanediol and menthyl pyrrolidone carboxylic acid are particularly preferred as skin-cooling active substances.

Preferred compositions according to the invention contain at least one skin-cooling active substance in total quantities of 0.01-1 wt. %, preferably 0.02-0.5 wt. % and particularly preferably 0.05-0.2 wt. %, based in each case on the total weight of the (propellant-free) composition.

Preferred compositions according to the invention are characterized in that at least one encapsulated active substance is contained. The active substances that can advantageously be encapsulated are, in particular, fragrances, perfume oils and/or skin-cooling active substances, but also other active skincare substances, such as vitamins, antioxidants etc.

Water-soluble polymers, such as starch, physically and/or chemically modified starches, cellulose derivatives, such as e.g. carboxymethyl cellulose, methyl cellulose, hydroxyethyl cellulose or hydroxypropyl methyl cellulose, carrageens, alginates, maltodextrins, dextrins, plant gums, pectins, xanthans, polyvinyl acetate and polyvinyl alcohol, polyvinyl pyrrolidine, polyamides, polyesters and homo- and copolymers of monomers selected from acrylic acid, methacrylic acid, maleic acid, fumaric acid, itaconic acid and the esters and salts of these acids, and any mixtures of these polymers, are preferred as the capsule material.

Preferred capsule materials are chemically modified starches, in particular aluminum starch octenylsuccinate, e.g.

the commercial product Dry Flo Plus from National Starch, or sodium starch octenylsuccinate, e.g. the commercial product Capsul from National Starch, and also carboxymethyl cellulose, carboxymethyl cellulose, methyl cellulose, hydroxyethyl cellulose and hydroxypropyl methyl cellulose, ethyl cellulose, e.g. the commercial product Tylose H 10 from Clariant, as well as carrageens, alginates and maltodextrins, and any mixtures of these polymers.

In another embodiment which is preferred according to the invention, the compositions according to the invention contain 0 to no more than 5 wt. % of ethanol.

Furthermore, the compositions according to the invention can contain additional active deodorant substances. As active deodorant substances, it is possible to use antimicrobial, antibacterial or bacteriostatic substances, antioxidants or odor adsorbants (e.g. zinc ricinoleate). Suitable antimicrobial, antibacterial or bacteriostatic substances are, in particular, organohalogen compounds and organohalides, quaternary ammonium compounds, a series of plant extracts and zinc compounds. Halogenated phenol derivatives are preferred, such as e.g. hexachlorophene or Irgasan DP 300 (triclosan, 2,4,4'-trichloro-2'-hydroxydiphenyl ether), 3,4,4'-trichlorocarbonilide, chlorhexidine (1,1'-hexamethylene-bis [5-(4-chlorophenyl)]biguanide), chlorhexidine gluconate, benzalkonium halides and cetylpyridinium chloride. In addition, sodium bicarbonate, sodium phenolsulfonate and zinc phenolsulfonate and e.g. the components of lime blossom oil can be used. Also more weakly effective antimicrobial substances, but which have a specific action against the gram-positive microbes responsible for the decomposition of sweat, can be used as active deodorant substances. Benzyl alcohol can also be used as an active deodorant substance. Other antibacterially effective deodorants are lantibiotics, glycoglycerolipids, sphingolipids (ceramides), sterols and other active substances that inhibit bacterial adhesion to the skin, e.g. glycosidases, lipases, proteases, carbohydrates, di- and oligosaccharide fatty acid esters and alkylated mono- and oligosaccharides. Preferred active deodorant substances are long-chain diols, e.g. 1,2-alkane($C_5$-$C_{18}$)diols, glycerol mono($C_8$-$C_{18}$) fatty acid esters or, particularly preferably, glycerol mono($C_6$-$C_{16}$)alkyl ethers, in particular 2-ethylhexyl glycerol ether, which are highly compatible with the skin and mucosa and are effective against corynebacteria, and also phenoxyethanol, phenoxyisopropanol (3-phenoxypropan-2-ol), anisyl alcohol, 2-methyl-5-phenylpentan-1-ol, 1,1-dimethyl-3-phenylpropan-1-ol, benzyl alcohol, 2-phenylethan-1-ol, 3-phenylpropan-1-ol, 4-phenylbutan-1-ol, 5-phenylpentan-1-ol, 2-benzylheptan-1-ol, 2,2-dimethyl-3-phenylpropan-1-ol, 2,2-dimethyl-3-(3'-methylphenyl)propan-1-ol, 2-ethyl-3-phenylpropan-1-ol, 2-ethyl-3-(3'-methylphenyl)propan-1-ol, 3-(3'-chlorophenyl)-2-ethylpropan-1-ol, 3-(2'-chlorophenyl)-2-ethylpropan-1-ol, 3-(4'-chlorophenyl)-2-ethylpropan-1-ol, 3-(3',4'-dichlorophenyl)-2-ethylpropan-1-ol, 2-ethyl-3-(2'-methylphenyl)propan-1-ol, 2-ethyl-3-(4'-methylphenyl)propan-1-ol, 3-(3',4'-dimethylphenyl)-2-ethylpropan-1-ol, 2-ethyl-3-(4'-methoxyphenyl)propan-1-ol, 3-(3',4'-dimethoxyphenyl)-2-ethylpropan-1-ol, 2-allyl-3-phenylpropan-1-ol and 2-n-pentyl-3-phenylpropan-1-ol.

Complex-forming substances can also support the deodorizing action by forming the heavy metal ions that have an oxidative catalytic action (e.g. iron or copper) into stable complexes. Suitable complexing agents are e.g. the salts of ethylenediaminetetraacetic acid or of nitrilotriacetic acid and the salts of 1-hydroxyethane-1,1-diphosphonic acid.

The compositions according to the invention, which are applied as a spray, are preferably formulated in accordance with the requirements of the desired spray application.

The compositions according to the invention are present in the form of a suspension, i.e. the active antiperspirant substance and optionally other insoluble components are suspended in a liquid carrier. Such a dispersed system should be shaken before application.

In a further preferred embodiment according to the invention, the compositions according to the invention are formulated as a suspension sprayable with a propellant.

Preferred compositions according to the invention can, for example, be packaged in pump or squeeze dispensers, in particular in multi-chamber pump or squeeze dispensers. Such dispensers use air, in particular ambient air, as propellant or deliver the composition according to the invention by pumps.

In another preferred embodiment of the invention, the composition is applied by means of a compressed or liquefied propellant.

All of the quantitative data relate, unless otherwise specified, to the weight of the propellant-free composition.

Packaging in a multi-chamber dispenser offers particular technical advantages.

The multi-chamber dispenser can also be used such that one chamber is filled with the composition according to the invention, while another chamber contains the compressed propellant. One such multi-chamber dispenser is for example a "bag-in can" package.

They two chambers may, however, also be connected to one another in such a manner that the composition according to the invention is divided into two sub-compositions which may simultaneously be discharged from the package, for example from separate orifices or from a single orifice.

Other preferred compositions according to the invention are characterized in that they are packaged with at least one propellant in a suitable pressure container.

Preferred propellants (propellant gases) according to the invention are selected from propane, propene, n-butane, isobutane, isobutene, n-pentane, pentene, iso-pentane, iso-pentene, methane, ethane, dimethyl ether, nitrogen, air, oxygen, laughing gas, dichlorofluoromethane, chlorodifluoromethane, chlorofluoromethane, 1,1,2,2-tetrachloro-1-fluoroethane, 1,1,1,2-tetrachloro-2-fluoroethane, 1,2,2-trichloro-1,1-difluoroethane, 1,1,2-trichloro-1,2-difluoroethane, 1,1,1-trichloro-2,2-difluoroethane, 2,2-dichloro-1,1,1-trifluoroethane, 1,2-dichloro-1,1,2-trifluoroethane, 2-chloro-1,1,1,2-tetrafluoroethane, 1-chloro-1,1,2,2-tetrafluoroethane, 1,1,2-trichloro-2-fluoroethane, 1,2-dichloro-1,2-difluoroethane, 1,2-dichloro-1,1-difluoroethane, 1-chloro-1,2,2-trifluoroethane, 2-chloro-1,1,1-trifluoroethane, 1-chloro-1,1,2-trifluoroethane, 1,2-dichloro-1-fluoroethane, 1,1-dichloro-1-fluoroethane, 2-chloro-1,1-difluoroethane, 1-chloro-1,1-difluoroethane, 1-chloro-2-fluoroethane, 1-chloro-1-fluoroethane, 2-chloro-1,1-difluoroethane, 1,1,1,3-tetrafluoroethane, heptafluoro-n-propane, perfluoroethane, monochlorodifluoromethane, 1,1-difluoroethane, both individually and in combination.

Propane, n-butane and isobutane are particularly preferred and mixtures of these propellants are particularly preferred. Furthermore preferred are also 1,1-difluoroethane, propane, n-butane, isobutane and mixtures of these propellants, in particular mixtures of 1,1-difluoroethane and n-butane.

Hydrophilic propellant gases, such as for example carbon dioxide, may advantageously be used for the purposes of the present invention if a small proportion of hydrophilic gases is selected and a lipophilic propellant gas (for example propane/ butane) is present in excess. Propane, n-butane, isobutane and mixtures of these propellant gases are particularly preferred. It has been found that it may be particularly preferred according to the invention to use n butane as the sole propellant gas.

The quantity of propellants is preferably 10 95 wt. %, particularly preferably 30 90 wt. % and extraordinarily preferably 60 86 wt. %, and furthermore extraordinarily preferably 70, 72, 74, 76, 78, 82, 84 or 85 wt. %, based in each case on the total weight of the preparation consisting of the suspension according to the invention and the propellant.

Vessels of metal (aluminum, tin plate, tin), of protected or non-splintering plastics or of glass coated on the outside with plastics may be considered as the pressurized gas container, the selection of which is made on the basis not only of pressure resistance and breaking strength, corrosion resistance, ease of filling but also of aesthetic considerations, ease of handling, printability etc. Special internal protection lacquers ensure corrosion resistance relative to the suspension according to the invention. One internal protection lacquer which is preferred according to the invention is an epoxy-phenol lacquer, as is obtainable inter alia with the name Hoba 7407 P. The valves that are used particularly preferably comprise an internally lacquered valve disc, the lacquer and valve material being mutually compatible. If aluminum valves are used, their valve discs may for example be coated on the inside with Micoflex lacquer. If tin plate valves are used according to the invention, their valve discs may for example be coated on the inside with PET (polyethylene terephthalate).

The cans are equipped with a suitable spray head. Depending on the spray head, output rates, based on completely full cans, of 0.1 g/s to 2.0 g/s are possible.

The present application also provides the use of at least one alkyl-modified polyether of the general formula ACTIVATOR-(I)

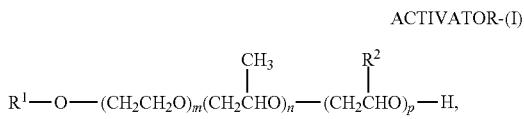

wherein $R^1$ signifies an aliphatic hydrocarbon residue with 1 to 3 C atoms, $R^2$ an aliphatic hydrocarbon residue with 8 to 30 C atoms, m a rational number from 10 to 50, n a rational number from 0 to 10 and p a rational number from 1 to 10, in an antiperspirant composition containing at least one active antiperspirant substance and 0-7 wt. %, preferably 0-3 wt. %, free water, for improving sweat reduction.

"Improving sweat reduction" is to be understood according to the invention as both a reduction of the amount of sweat and an acceleration of the release of the active antiperspirant substance from the composition according to the invention.

The present application also provides the use of at least one alkyl-modified polyether of the general formula ACTIVATOR-(I)

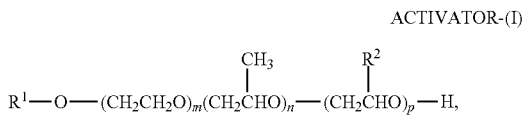

wherein $R^1$ signifies an aliphatic hydrocarbon residue with 1 to 3 C atoms, $R^2$ an aliphatic hydrocarbon residue with 8 to 30 C atoms, m a rational number from 10 to 50, n a rational number from 0 to 10 and p a rational number from 1 to 10, in an antiperspirant composition containing at least one active antiperspirant substance and 0-7 wt. %, preferably 0-3 wt. %, free water, for improving sweat reduction, wherein the alkyl-modified polyether is present in a composition according to one of claims 1-12.

The present application also provides the non-therapeutic, cosmetic use of an antiperspirant composition according to claim 1, 2, 3, 4, 5, 6, 7, 8, 9, 10, 11 or 12 for reducing and/or regulating perspiration and/or body odor.

With regard to other preferred embodiments of the uses according to the invention, the statements made relating to the compositions according to the invention apply mutatis mutandis.

The present application also provides a non-therapeutic, cosmetic method of reducing and/or regulating sweat formation and/or body odor, in which a composition according to the invention or a composition that is preferred according to the invention according to one of claim 1, 2, 3, 4, 5, 6, 7, 8, 9, 10, 11 or 12 is applied in an effective quantity onto the skin, preferably onto the skin in the arm pit area.

With regard to other preferred embodiments of the method according to the invention, the statements made relating to the compositions according to the invention apply mutatis mutandis.

The following tables show the composition of some preferred compositions according to the invention (all quantitative data are in wt. %, based on the total weight of the propellant-free composition):

|  | 1 | 2 | 3 | 4 |
| --- | --- | --- | --- | --- |
| Active antiperspirant substance (USP) | 5.0 to 40 | 10 to 35 | 15 to 28 | 23 to 27 |
| Liquid oil as carrier | 30 to 95 | 40 to 93 | 50 to 90 | 55 to 85 |
| Free water | 0 to 7 | 0 to 7 | 0 to 3 | 0 to 3 |
| ACTIVATOR-(I)* | 0.01 to 5 | 0.1 to 3 | 0.5 to 2 | 1 to 1.5 |

*wherein
$R^1$ is an aliphatic hydrocarbon residue with 1 to 3 C atoms,
$R^2$ is an aliphatic hydrocarbon residue with 8 to 30 C atoms,
m is a rational number from 10 to 50,
n is a rational number from 0 to 10,
p is a rational number from 1 to 10.

|  | 5 | 6 | 7 | 8 |
| --- | --- | --- | --- | --- |
| Antiperspirant aluminum salt (USP) | 5.0 to 40 | 10 to 35 | 15 to 28 | 23 to 27 |
| Liquid oil as carrier | 30 to 95 | 40 to 93 | 50 to 90 | 55 to 85 |
| Free water | 0 to 7 | 0 to 7 | 0 to 3 | 0 to 3 |
| ACTIVATOR-(I)* | 0.01 to 5 | 0.1 to 3 | 0.5 to 2 | 1 to 1.5 |

*wherein
$R^1$ is an aliphatic hydrocarbon residue with 1 to 3 C atoms,
$R^2$ is an aliphatic hydrocarbon residue with 8 to 30 C atoms,
m is a rational number from 10 to 50,
n is a rational number from 0 to 10,
p is a rational number from 1 to 10.

|  | 9 | 10 | 11 | 12 |
| --- | --- | --- | --- | --- |
| Antiperspirant aluminum salt (USP) | 5.0 to 40 | 10 to 35 | 15 to 28 | 23 to 27 |

|  | 9 | 10 | 11 | 12 |
|---|---|---|---|---|
| Liquid oil as carrier | 30 to 95 | 40 to 93 | 50 to 90 | 55 to 85 |
| Free water | 0 to 7 | 0 to 7 | 0 to 3 | 0 to 3 |
| ACTIVATOR-(I)** | 0.01 to 5 | 0.1 to 3 | 0.5 to 2 | 1 to 1.5 |

**wherein
$R^1$ is a methyl group,
$R^2$ is an n-decyl group,
m is a rational number from 21 to 23,
n = 0,

|  | 13 | 14 | 15 | 16 |
|---|---|---|---|---|
| Antiperspirant aluminum salt (USP) | 5.0 to 40 | 10 to 35 | 15 to 28 | 23 to 27 |
| Liquid oil as carrier | 30 to 95 | 40 to 93 | 50 to 90 | 55 to 85 |
| Free water | 0 to 7 | 0 to 7 | 0 to 3 | 0 to 3 |
| Methoxy PEG-22/ Dodecyl Glycol Copolymer | 0.01 to 5 | 0.1 to 3 | 0.5 to 2 | 1 to 1.5 |

|  | 17 | 18 | 19 | 20 |
|---|---|---|---|---|
| Antiperspirant aluminum salt (USP) | 5.0 to 40 | 10 to 35 | 15 to 28 | 23 to 27 |
| Volatile cyclic silicone oils (cyclomethicones) | 30 to 95 | 40 to 93 | 50 to 90 | 55 to 85 |
| Free water | 0 to 7 | 0 to 7 | 0 to 3 | 0 to 3 |
| ACTIVATOR-(I)** | 0.01 to 5 | 0.1 to 3 | 0.5 to 2 | 1 to 1.5 |

**wherein
$R^1$ is a methyl group,
$R^2$ is an n-decyl group,
m is a rational number from 21 to 23,
n = 0,
p is a rational number from 4 to 8.

|  | 21 | 22 | 23 | 24 |
|---|---|---|---|---|
| Antiperspirant aluminum salt (USP) | 5.0 to 40 | 10 to 35 | 15 to 28 | 23 to 27 |
| Volatile cyclic silicone oils (cyclomethicones) | 30 to 95 | 40 to 93 | 50 to 90 | 55 to 85 |
| Free water | 0 to 7 | 0 to 7 | 0 to 3 | 0 to 3 |
| Methoxy PEG-22/ Dodecyl Glycol Copolymer | 0.01 to 5 | 0.1 to 3 | 0.5 to 2 | 1 to 1.5 |

|  | 25 | 26 | 27 | 28 |
|---|---|---|---|---|
| Antiperspirant aluminum salt (USP) | 5.0 to 40 | 10 to 35 | 15 to 28 | 23 to 27 |
| Volatile linear polydimethyl siloxanes with 2 to 10 siloxane units | 30 to 95 | 40 to 93 | 50 to 90 | 55 to 85 |
| Free water | 0 to 7 | 0 to 7 | 0 to 3 | 0 to 3 |
| ACTIVATOR-(I)** | 0.01 to 5 | 0.1 to 3 | 0.5 to 2 | 1 to 1.5 |

**wherein
$R^1$ is a methyl group,
$R^2$ is an n-decyl group,
m is a rational number from 21 to 23,
n = 0,
p is a rational number from 4 to 8.

|  | 29 | 30 | 31 | 32 |
|---|---|---|---|---|
| Antiperspirant aluminum salt (USP) | 5.0 to 40 | 10 to 35 | 15 to 28 | 23 to 27 |
| Volatile linear polydimethyl siloxanes with 2 to 10 siloxane units | 30 to 95 | 40 to 93 | 50 to 90 | 55 to 85 |
| Free water | 0 to 7 | 0 to 7 | 0 to 3 | 0 to 3 |
| Methoxy PEG-22/ Dodecyl Glycol Copolymer | 0.01 to 5 | 0.1 to 3 | 0.5 to 2 | 1 to 1.5 |

|  | 33 | 34 | 35 | 36 |
|---|---|---|---|---|
| Antiperspirant aluminum salt (USP) | 5.0 to 40 | 10 to 35 | 15 to 28 | 23 to 27 |
| i) Ester oil, selected from 2-ethylhexyl palmitate, isopropyl myristate and isopropyl palmitate, and ii) at least one isoparaffin oil, selected from isodecane, isoundecane, isododecane, isotridecane, isotetradecane, isopentadecane, isohexadecane and isoeicosane, and iii) 0 to no more than 1 wt. % of cyclomethicone | 30 to 95 | 40 to 93 | 50 to 90 | 55 to 85 |
| Free water | 0 to 7 | 0 to 7 | 0 to 3 | 0 to 3 |
| ACTIVATOR-(I)** | 0.01 to 5 | 0.1 to 3 | 0.5 to 2 | 1 to 1.5 |

**wherein
$R^1$ is a methyl group,
$R^2$ is an n-decyl group,
m is a rational number from 21 to 23,
n = 0,
p is a rational number from 4 to 8.

|  | 37 | 38 | 39 | 40 |
|---|---|---|---|---|
| Antiperspirant aluminum salt (USP) | 5.0 to 40 | 10 to 35 | 15 to 28 | 23 to 27 |
| i) Ester oil, selected from 2-ethylhexyl palmitate, isopropyl myristate and isopropyl palmitate, and ii) at least one isoparaffin oil, selected from isodecane, isoundecane, isododecane, isotridecane, | 30 to 95 | 40 to 93 | 50 to 90 | 55 to 85 |

-continued

|  | 37 | 38 | 39 | 40 |
|---|---|---|---|---|
| isotetradecane, isopentadecane, isohexadecane and isoeicosane, and | | | | |
| iii) 0 to no more than 1 wt. % of cyclomethicone | | | | |
| Free water | 0 to 7 | 0 to 7 | 0 to 3 | 0 to 3 |
| Methoxy PEG-22/Dodecyl Glycol Copolymer | 0.01 to 5 | 0.1 to 3 | 0.5 to 2 | 1 to 1.5 |

|  | 41 | 42 | 43 | 44 |
|---|---|---|---|---|
| Antiperspirant aluminum salt (USP) | 5.0 to 40 | 10 to 35 | 15 to 28 | 23 to 27 |
| Triethyl citrate/ester/$C_{10}$-$C_{13}$ isoparaffin | 30 to 95 | 40 to 93 | 50 to 90 | 55 to 85 |
| Free water | 0 to 7 | 0 to 7 | 0 to 3 | 0 to 3 |
| ACTIVATOR-(I)** | 0.01 to 5 | 0.1 to 3 | 0.5 to 2 | 1 to 1.5 |

**wherein
$R^1$ is a methyl group,
$R^2$ is an n-decyl group,
m is a rational number from 21 to 23,
n = 0,
p is a rational number from 4 to 8.

|  | 45 | 46 | 47 | 48 |
|---|---|---|---|---|
| Antiperspirant aluminum salt (USP) | 5.0 to 40 | 10 to 35 | 15 to 28 | 23 to 27 |
| Triethyl citrate/ester/$C_{10}$-$C_{13}$ isoparaffin | 30 to 95 | 40 to 93 | 50 to 90 | 55 to 85 |
| Free water | 0 to 7 | 0 to 7 | 0 to 3 | 0 to 3 |
| Methoxy PEG-22/Dodecyl Glycol Copolymer | 0.01 to 5 | 0.1 to 3 | 0.5 to 2 | 1 to 1.5 |

|  | 49 | 50 | 51 | 52 |
|---|---|---|---|---|
| Antiperspirant aluminum salt (USP) | 5.0 to 40 | 10 to 35 | 15 to 28 | 23 to 27 |
| Triethyl citrate/ester/$C_{10}$-$C_{13}$ isoparaffin | 30 to 95 | 40 to 93 | 50 to 90 | 55 to 85 |
| Free water | 0 to 7 | 0 to 7 | 0 to 3 | 0 to 3 |
| ACTIVATOR-(I)** | 0.01 to 5 | 0.1 to 3 | 0.5 to 2 | 1 to 1.5 |
| Cyclomethicone | 0 to 2 | 0 to 2 | 0 to 1 | 0 to 1 |

**wherein
$R^1$ is a methyl group,
$R^2$ is an n-decyl group,
m is a rational number from 21 to 23,
n = 0,
p is a rational number from 4 to 8.

|  | 53 | 54 | 55 | 56 |
|---|---|---|---|---|
| Antiperspirant aluminum salt (USP) | 5.0 to 40 | 10 to 35 | 15 to 28 | 23 to 27 |
| Triethyl citrate/ester/$C_{10}$-$C_{13}$ isoparaffin | 30 to 95 | 40 to 93 | 50 to 90 | 55 to 85 |
| Free water | 0 to 7 | 0 to 7 | 0 to 3 | 0 to 3 |
| Methoxy PEG-22/Dodecyl Glycol Copolymer | 0.01 to 5 | 0.1 to 3 | 0.5 to 2 | 1 to 1.5 |
| Cyclomethicone | 0 to 2 | 0 to 2 | 0 to 1 | 0 to 1 |

|  | 57 | 58 | 59 | 60 |
|---|---|---|---|---|
| Antiperspirant aluminum salt (USP) | 5.0 to 40 | 10 to 35 | 15 to 28 | 23 to 27 |
| Triethyl citrate/ester/$C_{10}$-$C_{13}$ isoparaffin | 30 to 95 | 40 to 93 | 50 to 90 | 55 to 85 |
| Free water | 0 to 7 | 0 to 7 | 0 to 3 | 0 to 3 |
| ACTIVATOR-(I)** | 0.01 to 5 | 0.1 to 3 | 0.5 to 2 | 1 to 1.5 |
| Cyclomethicone | 0 to 2 | 0 to 2 | 0 to 1 | 0 to 1 |
| Hydrophobically modified clay mineral | 0.5 to 10 | 1 to 7 | 2 to 6 | 3 to 5 |

**wherein
$R^1$ is a methyl group,
$R^2$ is an n-decyl group,
m is a rational number from 21 to 23,
n = 0,
p is a rational number from 4 to 8.

|  | 61 | 62 | 63 | 64 |
|---|---|---|---|---|
| Antiperspirant aluminum salt (USP) | 5.0 to 40 | 10 to 35 | 15 to 28 | 23 to 27 |
| Triethyl citrate/ester/$C_{10}$-$C_{13}$ isoparaffin | 30 to 95 | 40 to 93 | 50 to 90 | 55 to 85 |
| Free water | 0 to 7 | 0 to 7 | 0 to 3 | 0 to 3 |
| Methoxy PEG-22/Dodecyl Glycol Copolymer | 0.01 to 5 | 0.1 to 3 | 0.5 to 2 | 1 to 1.5 |
| Cyclomethicone | 0 to 2 | 0 to 2 | 0 to 1 | 0 to 1 |
| Hydrophobically modified clay mineral | 0.5 to 10 | 1 to 7 | 2 to 6 | 3 to 5 |

The antiperspirant suspension compositions 1-64 according to the invention listed above (package contents) were packaged in spray cans made of internally lacquered aluminum or tin plate (lacquered and unlacquered) and pressurized with an isobutane/butane/propane propellant mixture in a weight ratio of suspension:propellant of 30:70, 25:75, 22:78, 20:80, 18:82, 15:85 and 13:87.

The following examples are intended to illustrate the invention without limiting it thereto. All quantitative data are in wt. %.

The antiperspirant suspension compositions 1-11 and 14 according to the invention (package contents) were packaged in spray cans made of internally lacquered aluminum or tin plate (lacquered and unlacquered) and pressurized with an isobutane/butane/propane propellant mixture in a weight ratio of suspension:propellant of 30:70, 25:75, 22:78, 20:80, 18:82, 15:85 and 13:87; the compositions according to the invention 12 and 13 were pressurized with an n-butane/1,1-difluoroethane propellant mixture in the weight ratio of suspension:propellant of 45:55, 40:60 and 30:70.

| INCI | No. 1 | No. 2 | No. 3 |
|---|---|---|---|
| Aluminum chlorohydrate (activated) USP | 10.0 | 22.0 | 25.0 |
| Water of crystallization (from ACH) | 2.0 | 4.4 | 5.0 |
| Disteardimonium Hectorite | 5.0 | 5.0 | 3.5 |
| Propylene carbonate | 1.0 | 1.0 | 1.2 |
| Perfume | 8.0 | 8.6 | 7.3 |
| Isopropyl myristate | 13.0 | 8.0 | 13.0 |
| Triethyl citrate | 15.0 | 10.0 | 14.0 |
| $C_{10}$-$C_{13}$ isoalkanes | 45.0 | 40.0 | 30.0 |
| Methoxy PEG-22/Dodecyl Glycol Copolymer (Elfacos E 200) | 1.0 | 1.0 | 1.0 |
| Total | 100.0 | 100.0 | 100.0 |
| Conductivity | moderate-good | moderate-good | moderate-good |

| INCI | No. 4 | No. 5 | No. 6 |
|---|---|---|---|
| Aluminum chlorohydrate (activated) USP | 10.0 | 22.0 | 25.0 |
| Water of crystallization (from ACH) | 2.0 | 4.4 | 5.0 |
| Disteardimonium Hectorite | 5.0 | 5.0 | 3.5 |
| Propylene carbonate | 1.0 | 1.0 | 1.2 |
| Perfume | 8.0 | 8.6 | 7.3 |
| Isopropyl myristate | 13.0 | 8.0 | 13.0 |
| Triethyl citrate | 14.0 | 9.0 | 13.0 |
| $C_{10}$-$C_{13}$ isoalkanes | 45.0 | 40.0 | 30.0 |
| Methoxy PEG-22/Dodecyl Glycol Copolymer (Elfacos E 200) | 2.0 | 2.0 | 2.0 |
| Total | 100.0 | 100.0 | 100.0 |
| Conductivity | good | good | good |

Measurement of Active Antiperspirant Substance Release

In order to ascertain whether the active antiperspirant substance is rapidly available, the time profile of the conductivity of the suspensions from a defined film is measured in a specific quantity of deionized water.

The value for conductivity reached at the end of the test is of the order of 25-160 microsiemens per centimeter [µS/cm] for the compositions according to the invention.

The compositions without Methoxy PEG-22/Dodecyl Glycol Copolymer exhibited a final conductivity of no more than 15 microsiemens per centimeter [µS/cm].

Inventive and comparison compositions no. 1 to no. 6 were applied onto the skin in the arm pit area.

A more rapid onset of antiperspirant action was observed for the compositions according to the invention.

A qualitative assessment of the tested compositions is noted down in the above tables on a rating scale from 1-5 with 1=very good, 5=poor. This assessment takes account not only of the final conductivity value achieved but also of the gradient of the change in conductivity over time at the start of the test. A steep gradient is interpreted to be synonymous with rapid release of the active antiperspirant substance.

Further Examples of Formulations According to the Invention

Weight Ratio of Package Contents to Propellant as in the Preceding Examples

| | No. 7 | No. 8 | No. 9 | No. 10 | No. 11 | No. 12 | No. 13 | No. 14 |
|---|---|---|---|---|---|---|---|---|
| Perfume | 5.0 | 5.0 | 7.00 | 5.0 | 5.0 | 5.0 | 7.0 | 5.0 |
| Aluminum chlorohydrate (activated), including water of crystallization | 32.0 | 28.0 | 26.0 | 35.0 | 32.0 | 32.0 | 30.0 | 28.0 |
| Encapsulated 2-benzylheptanol, phenoxyethanol (Na starch octenyl succinate, mannitol, silica) | 2.0 | — | — | 2.0 | 1.0 | — | 1.0 | — |
| Methoxy PEG-22/Dodecyl Glycol Copolymer (Elfacos E 200) | 1.0 | 1.0 | 2.0 | 2.0 | 2.0 | 1.5 | 1.5 | 1.5 |
| Isopropyl palmitate | — | — | — | — | — | 5.0 | — | — |
| $C_{10-13}$ isoparaffin | 25.0 | 30.0 | 25.0 | — | — | — | — | — |
| $C_{12-15}$ alkyl benzoate | — | — | — | 5.0 | 5.0 | — | — | — |
| Cosmacol PLG | — | — | — | — | 5.0 | 5.0 | 5.0 | — |
| Disteardimonium Hectorite | 4.5 | 3.9 | 4.0 | 3.8 | 5.0 | 4.5 | — | 3.9 |
| Propylene carbonate | 1.5 | 1.3 | 1.0 | 1.3 | 1.70 | 1.5 | — | 1.3 |
| Silica | — | — | — | — | — | 0.8 | 0.8 | — |
| Silica dimethyl silylate | — | — | — | — | — | 1.0 | 1.0 | — |
| Tocopheryl acetate | 0.2 | — | 0.5 | 0.1 | — | — | — | — |
| Cyclopentasiloxane | — | — | — | ad 100 | ad 100 | ad 100 | ad 100 | ad 100 |
| Isopropyl myristate | — | ad 100 | — | — | — | — | — | 5.0 |
| 2-Ethylhexyl palmitate | ad 100 | — | ad 100 | — | — | — | — | — |

Cosmacol PLG (INCI: DI-C12-13 ALKYL TARTRATE, TRI-C12-13 ALKYL CITRATE, SILICA)

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An antiperspirant composition for personal body care, made up as a suspension which is sprayable with or without a propellant, comprising:
   a) at least one active antiperspirant substance;
   b) at least one oil which is liquid at 20° C. and 1013.25 mbar as carrier;
   c) 0-7 wt. % free water, based on the weight of the propellant-free composition; and
   d) at least one alkyl-modified polyether of the general formula ACTIVATOR-(I):

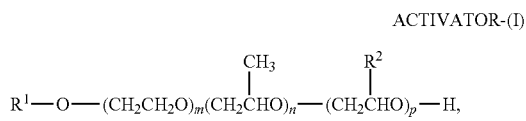

wherein
   $R^1$ signifies an aliphatic hydrocarbon residue with 1 to 3 C atoms,
   $R^2$ signifies an aliphatic hydrocarbon residue with 8 to 30 C atoms,
   m is a rational number from 10 to 50,
   n is a rational number from 0 to 10, and
   p is a rational number from 1 to 10.

2. The composition according to claim 1, wherein the alkyl-modified polyether d) is selected from compounds of the general formula ACTIVATOR-(I), wherein
   $R^1$ is selected from a methyl group, an ethyl group, an n-propyl group and a 1-methylethyl group,
   $R^2$ is selected from an n-octyl, 2-ethylhexyl, n-nonyl, n-decyl, 2-ethyloctyl, n-undecyl, n-dodecyl, 2-ethyldecyl, n-tridecyl, myristyl, n-pentadecyl, cetyl, palmityl, stearyl, elaidyl, arachidyl, behenyl or cocyl group,
   m represents a number from 12-30,
   n represents a rational number from 0-8, and
   p represents a rational number from 1-9.

3. The composition according to claim 1, wherein the alkyl-modified polyether d) of the general formula ACTIVATOR-(I) has an HLB value in the range of 5-7.

4. The composition according to claim 1, wherein at least one alkyl-modified polyether of the general formula ACTIVATOR-(I) has an HLB value in the range of 5-7, and wherein $R^1$=methyl, $R^2$=n-decyl, m=22, n=0 and p=4-5.

5. The composition according to claim 1, wherein at least one alkyl-modified polyether of the general formula ACTIVATOR-(I) is contained with an HLB value in the range of 5-7, and wherein $R^1$=methyl, $R^2$=n-decyl, m=22, n=0 and p=7-8.

6. The composition according to claim 1, wherein the alkyl-modified polyether d) of the general formula ACTIVATOR-(I) is selected from compounds with the INCI name Methoxy PEG-22/Dodecyl Glycol Copolymer.

7. The composition according to claim 1, wherein the at least one carrier oil b) is selected from the group consisting of volatile cyclic or linear silicone oils, non-volatile higher molecular-weight linear dimethyl polysiloxanes, esters of linear or branched saturated or unsaturated fatty alcohols having 2-30 carbon atoms with linear or branched saturated or unsaturated fatty acids having 2-30 carbon atoms, which may be hydroxylated, benzoic acid esters of linear or branched $C_{8-22}$ alkanols, $C_8$-$C_{22}$ fatty alcohol esters of monohydric or polyhydric $C_2$-$C_7$ hydroxycarboxylic acids, the addition products of ethylene oxide and/or propylene oxide to monohydric or polyhydric $C_{3-20}$ alkanols, liquid paraffin oils, isoparaffin oils, synthetic hydrocarbons, branched saturated or unsaturated fatty alcohols with 6-30 carbon atoms, mixtures of Guerbet alcohols and Guerbet alcohol esters, the symmetrical, asymmetrical or cyclic esters of carbonic acid with fatty alcohols, triglycerides of linear or branched, saturated or unsaturated, optionally hydroxylated $C_{8-30}$ fatty acids, dicarboxylic acid esters of linear or branched $C_2$-$C_{10}$ alkanols, di-n-alkyl ethers with a total of 12 to 36 C atoms, and mixtures thereof.

8. The composition according to claim 1, wherein the at least one carrier oil b) which is liquid under normal conditions comprises at least one isoparaffin oil selected from the group consisting of isodecane, isoundecane, isododecane, isotridecane, isotetradecane, isopentadecane, isohexadecane and isoeicosane.

9. The composition according to claim 1, comprising from 0 to no more than 1 wt. % of cyclomethicones.

10. The composition according to claim 1, wherein the carrier oil b) which is liquid under normal conditions consists of a mixture of b)i) an ester oil, selected from 2-ethylhexyl palmitate, isopropyl myristate and isopropyl palmitate, and b)ii) at least one isoparaffin oil, selected from isodecane, isoundecane, isododecane, isotridecane, isotetradecane, isopentadecane, isohexadecane and isoeicosane, and b)iii) 0 to no more than 1 wt. % of cyclomethicone.

11. The composition according to claim 1, formulated as a suspension or solution sprayable with a propellant.

12. The composition according to claim 11, comprising a weight ratio of propellant to propellant-free composition of 20:80 to 95:5.

13. A non-therapeutic, cosmetic method of reducing and/or regulating sweat formation and/or body odor, in which a composition according to claim 1 is applied onto the skin in an effective quantity.

* * * * *